US009400280B2

(12) United States Patent
Hartman

(10) Patent No.: US 9,400,280 B2
(45) Date of Patent: Jul. 26, 2016

(54) PIPERIDINE DERIVATIVES AND METHODS OF TREATING HEPATITIS B INFECTIONS

(71) Applicant: Novira Therapeutics, Inc., Doylestown, PA (US)

(72) Inventor: George D. Hartman, Lansdale, PA (US)

(73) Assignee: NOVIRA THERAPEUTICS, INC., Doylestown, PA (US)

( * ) Notice: Subject to any disclaimer, the term of this patent is extended or adjusted under 35 U.S.C. 154(b) by 0 days.

(21) Appl. No.: 14/670,001

(22) Filed: Mar. 26, 2015

(65) Prior Publication Data

US 2015/0274652 A1    Oct. 1, 2015

Related U.S. Application Data

(60) Provisional application No. 61/971,070, filed on Mar. 27, 2014.

(51) Int. Cl.
| | |
|---|---|
| *C07D 211/96* | (2006.01) |
| *G01N 33/569* | (2006.01) |
| *A61K 31/445* | (2006.01) |
| *A61K 31/5375* | (2006.01) |
| *A61K 31/54* | (2006.01) |
| *C07D 491/048* | (2006.01) |
| *A61K 31/4355* | (2006.01) |
| *A61K 45/06* | (2006.01) |
| *A61K 31/4453* | (2006.01) |
| *A61K 31/506* | (2006.01) |

(52) U.S. Cl.
CPC ...... *G01N 33/56988* (2013.01); *A61K 31/4355* (2013.01); *A61K 31/445* (2013.01); *A61K 31/4453* (2013.01); *A61K 31/506* (2013.01); *A61K 31/5375* (2013.01); *A61K 31/54* (2013.01); *A61K 45/06* (2013.01); *C07D 211/96* (2013.01); *C07D 491/048* (2013.01)

(58) Field of Classification Search
CPC .................................................. C07D 211/96
See application file for complete search history.

(56) References Cited

U.S. PATENT DOCUMENTS

| | | | |
|---|---|---|---|
| 4,569,940 A | 2/1986 | Watts | |
| 5,272,167 A | 12/1993 | Girijavallabhan et al. | |
| 5,607,929 A | 3/1997 | Nicol | |
| 5,919,970 A | 7/1999 | Song et al. | |
| 5,939,423 A | 8/1999 | Karlin | |
| 6,650,463 B2 | 11/2003 | Obikawa et al. | |
| 7,186,735 B2 | 3/2007 | Strobel et al. | |
| 7,338,956 B2 | 3/2008 | Strobel et al. | |
| 7,595,322 B2 | 9/2009 | Morgan et al. | |
| 7,750,158 B2 | 7/2010 | Shankar et al. | |
| 7,888,373 B2 | 2/2011 | Morgan et al. | |
| 8,084,457 B2 | 12/2011 | Choidas et al. | |
| 8,097,728 B2 | 1/2012 | Gu et al. | |
| 8,101,620 B2 | 1/2012 | Morgan et al. | |
| 8,153,803 B2 | 4/2012 | Kazantsev et al. | |
| 8,404,747 B2 | 3/2013 | Kazantsev et al. | |
| 8,609,668 B2 | 12/2013 | Cuconati et al. | |
| 8,629,274 B2 | 1/2014 | Hartman et al. | |
| 8,993,771 B2 | 3/2015 | Hartman et al. | |
| 9,061,008 B2 | 6/2015 | Hartman et al. | |
| 9,066,932 B2 | 6/2015 | Hartman et al. | |
| 2004/0039009 A1 | 2/2004 | Jagtap et al. | |
| 2005/0009871 A1 | 1/2005 | Ramesh et al. | |
| 2005/0054850 A1 | 3/2005 | Wu et al. | |
| 2005/0239833 A1 | 10/2005 | Kazantsev et al. | |
| 2007/0142440 A1 | 6/2007 | Burgdorf et al. | |
| 2009/0163545 A1 | 6/2009 | Goldfarb | |
| 2011/0009622 A1 | 1/2011 | Jitsuoka et al. | |
| 2011/0184019 A1 | 7/2011 | Zitzmann et al. | |
| 2011/0189771 A1 | 8/2011 | Block et al. | |
| 2011/0275630 A1 | 11/2011 | Matulenko et al. | |
| 2013/0142827 A1 | 6/2013 | Block et al. | |
| 2013/0267517 A1 | 10/2013 | Guo et al. | |
| 2013/0303552 A1 | 11/2013 | Xu et al. | |

FOREIGN PATENT DOCUMENTS

| | | |
|---|---|---|
| CN | 102093320 A | 6/2011 |
| EP | 0 742 200 B1 | 7/1999 |
| EP | 2 280 001 A1 | 2/2011 |
| WO | 84/03281 A1 | 8/1984 |
| WO | 99/38845 A1 | 8/1999 |
| WO | 99/48492 A1 | 9/1999 |
| WO | 99/65906 A1 | 12/1999 |
| WO | 01/05390 A2 | 1/2001 |
| WO | 01/19788 A2 | 3/2001 |
| WO | 01/55121 A1 | 8/2001 |
| WO | 01/85694 A2 | 11/2001 |
| WO | 02/051410 A2 | 7/2002 |
| WO | 03/007955 A2 | 1/2003 |

(Continued)

OTHER PUBLICATIONS

Campagna et al. (Apr. 10, 2013) "Sulfonamoylbenzamides Derivatives Inhibit the Assembly of Hepatitis B virus in Nucleocapsids," 87(12):6931-6942.
El-Sharief et al. (1987) "Synthesis of different types of chlorinated sulfonamides with expected insecticidal and bactericidal activities," Proceedings of the Indian National Science Academy, Part A: Physical Sciences. 53 (1):179-188.
International Search Report corresponding to International Patent Application No. PCT/US2012/071195, mailed Dec. 21, 2012.
Lambeng et al. (2007) "Arylsulfonannides as a new class of cannabinoid CB1 receptor ligands: Identification of a lead and initial SAR studies," Bioorganic & Medicinal Chemistry Letters. 17(1):272-277.
Mohamed et al. (1986) "Synthesis of different types of chlorinated sulfonamides with expected insecticidal and antimicrobial activities," Acta Pharmaceutica Jugoslavica. 36(3):301-310.
Ermann et al. (2008) "Arylsulfonamide CB2 receptor agonists: SAR and optimization of CB2 selectivity," Bioorganic & Medicinal Chemistry Letters. 18(5):1725-1729.

(Continued)

*Primary Examiner* — David K O Dell
(74) *Attorney, Agent, or Firm* — Lathrop & Gage LLP; Brian C. Trinque; Benjamin D. Heuberger

(57) ABSTRACT

Provided herein are compounds useful for the treatment of HBV infection in a subject in need thereof, pharmaceutical compositions thereof, and methods of inhibiting, suppressing, or preventing HBV infection in the subject.

9 Claims, No Drawings

(56) References Cited

FOREIGN PATENT DOCUMENTS

| | | |
|---|---|---|
| WO | 03/044016 A1 | 5/2003 |
| WO | 2004/022060 A2 | 3/2004 |
| WO | 2004/058709 A1 | 7/2004 |
| WO | 2004/086865 A1 | 11/2004 |
| WO | 2004/099192 A2 | 11/2004 |
| WO | 2005/016922 A2 | 2/2005 |
| WO | 2004/100947 A2 | 3/2005 |
| WO | 2005/044797 A1 | 5/2005 |
| WO | 2005/087217 A1 | 9/2005 |
| WO | 2005/105785 A2 | 11/2005 |
| WO | 2005/115374 A1 | 12/2005 |
| WO | 2006/002133 A1 | 1/2006 |
| WO | 2006/024834 A1 | 3/2006 |
| WO | 2006/053109 A1 | 5/2006 |
| WO | 2006/067445 A2 | 6/2006 |
| WO | 2006/067446 A1 | 6/2006 |
| WO | 2006/123257 A2 | 11/2006 |
| WO | 2006/128129 A2 | 11/2006 |
| WO | 2006/128172 A2 | 11/2006 |
| WO | 2007/031791 A1 | 3/2007 |
| WO | 2008/022171 A1 | 2/2008 |
| WO | 2008/093614 A1 | 8/2008 |
| WO | 2008/137794 A1 | 11/2008 |
| WO | 2009/016088 A1 | 2/2009 |
| WO | 2009/062402 A1 | 5/2009 |
| WO | 2009/086303 A2 | 7/2009 |
| WO | 2009/131065 A1 | 10/2009 |
| WO | 2010/018113 A2 | 2/2010 |
| WO | 2010/043592 A1 | 4/2010 |
| WO | 2010/088000 A2 | 8/2010 |
| WO | 2010/123139 A1 | 10/2010 |
| WO | 2011/002635 A1 | 1/2011 |
| WO | 2011/088015 A1 | 7/2011 |
| WO | 2011/088561 A1 | 7/2011 |
| WO | 2011/109237 A2 | 9/2011 |
| WO | 2011/112191 A1 | 9/2011 |
| WO | 2011/123609 A1 | 10/2011 |
| WO | 2011/155898 A1 | 12/2011 |
| WO | 2012/016133 A2 | 2/2012 |
| WO | 2012/018635 A2 | 2/2012 |
| WO | 2012/075235 A1 | 6/2012 |
| WO | 2012/080050 A1 | 6/2012 |
| WO | 2012/136834 A1 | 10/2012 |
| WO | 2013/006394 A1 | 1/2013 |
| WO | 2013/102655 A1 | 7/2013 |
| WO | 2013/130703 A2 | 9/2013 |
| WO | 2013/181584 A2 | 12/2013 |
| WO | 2014/033167 A1 | 3/2014 |
| WO | 2014/033170 A1 | 3/2014 |
| WO | 2014/033176 A1 | 3/2014 |
| WO | 2014/037480 A1 | 3/2014 |
| WO | 2014/106019 A2 | 7/2014 |

OTHER PUBLICATIONS

Taylor et al. (Mar. 2011) "A Brain-Permeable Small Molecule Reduces Neuronal Cholesterol by Inhibiting Activity of Sirtuin 2 Deacetylase," ACS Chemical Biology. 6:540-546.

Duan et al. (2009) "2-Phenylquinazolin-4(3H)-one, a class of potent PDE5 inhibitors with high selectivity versus PDE6," Bioorganic and Medicinal Chemistry. 19(10):2777-2779.

Search Report with Written Opinion corresponding to Singapore Patent Application No. 11201402660Y, completed May 22, 2015.

Supplementary European Search Report corresponding to European Patent Application No. 12859684, dated May 27, 2015.

Kim et al. (Apr. 9, 2011) "Discovery of novel HCV polymerase inhibitors using pharmacophore-based virtual screening," Bioorganic and Medicinal Chemistry. 21(11):3329-3334.

Patel, N.B. and Rathod, R.D., "Synthesis N-ethylpiperazinyl Sulfonyl Group Incorporated Benzamides" 2005, Indian Journal of Heterocyclic Chemistry, V15, Oct.-Dec., pp. 201-202.

PIPERIDINE DERIVATIVES AND METHODS OF TREATING HEPATITIS B INFECTIONS

RELATED APPLICATION

This application claims priority to U.S. Provisional Application No. 61/971,070, filed on Mar. 27, 2014, the entire contents of which are incorporated herein in its entirety.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

Provided herein are compounds useful for the treatment of HBV infection in a subject in need thereof.

In one aspect, provided herein are compounds having the Formula I:

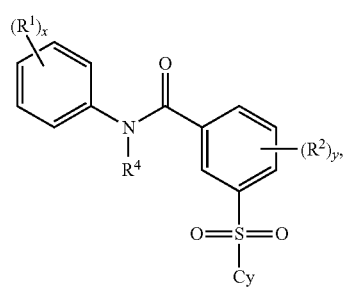

I or a pharmaceutically acceptable salt thereof.

In one embodiment, the compound of Formula I has the Formula II:

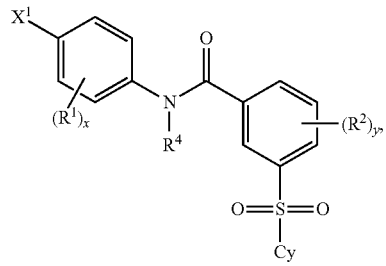

II or a pharmaceutically acceptable salt thereof.

In another embodiment, the compound of Formula I has the Formula III:

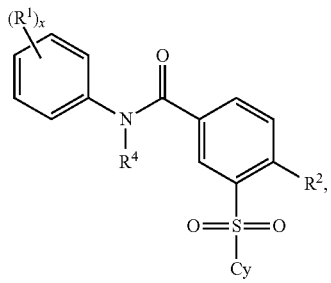

III or a pharmaceutically acceptable salt thereof.

In another aspect, provided herein are compounds having the Formula IV:

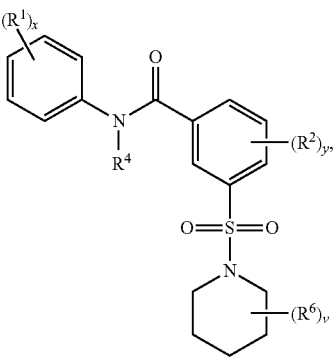

IV or a pharmaceutically acceptable salt thereof.

In another aspect, provided herein are pharmaceutical compositions comprising a compound of Formula I, II, III, or IV, or a pharmaceutically acceptable salt thereof, together with a pharmaceutically acceptable carrier.

In one aspect, provided herein is a method of treating an HBV infection in an individual in need thereof, comprising administering to the individual a therapeutically effective amount of a compound of Formula I, II, III, or IV.

In another aspect, provided herein is a method of eradicating an HBV infection in an individual in need thereof, comprising administering to the individual a therapeutically effective amount of a compound of Formula I, II, III, or IV.

In another aspect, provided herein is a method of reducing viral load associated with an HBV infection in an individual in need thereof, comprising administering to the individual a therapeutically effective amount of a compound of Formula I, II, III, or IV.

In still another aspect, provided herein is a method of reducing reoccurrence of an HBV infection in an individual in need thereof, comprising administering to the individual a therapeutically effective amount of a compound of Formula I, II, III, or IV.

In yet another aspect, provided herein is a method of reducing an adverse physiological impact of an HBV infection in an individual in need thereof, comprising administering to the individual a therapeutically effective amount of a compound of Formula I, II, III, or IV.

Also provided herein are methods of inducing remission of hepatic injury from an HBV infection in an individual in need thereof, comprising administering to the individual a therapeutically effective amount of a compound of Formula I, II, III, or IV.

In another aspect, provided herein is a method of reducing the physiological impact of long-term antiviral therapy for HBV infection in an individual in need thereof, comprising administering to the individual a therapeutically effective amount of a compound of Formula I, II, III, or IV.

In another aspect, provided herein is method of prophylactically treating an HBV infection in an individual in need thereof, wherein the individual is afflicted with a latent HBV infection, comprising administering to the individual a therapeutically effective amount of a compound of Formula I, II, III, or IV.

Any of the above methods may further comprise administration to the individual at least one additional therapeutic agent. In an embodiment, the additional therapeutic agent is selected from the group consisting of a HBV polymerase inhibitor, interferon, viral entry inhibitor, viral maturation inhibitor, literature-described capsid assembly modulator, reverse transcriptase inhibitor, a TLR-agonist, and agents of distinct or unknown mechanism, and a combination thereof.

In another embodiment, the additional therapeutic agent is a reverse transcriptase inhibitor and is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the additional therapeutic agent is a TLR agonist. In a preferred embodiment, the TLR agonist is a TLR-7 agonist selected from the group consisting of SM360320 (9-benzyl-8-hydroxy-2-(2-methoxy-ethoxy)adenine) and AZD 8848 (methyl[3-({[3-(6-amino-2-butoxy-8-oxo-7,8-dihydro-9H-purin-9-yl)propyl][3-(4-morpholinyl)propyl]amino}methyl) phenyl]acetate).

In a further embodiment of the combination therapy, the additional therapeutic agent is an interferon, wherein the interferon is any interferon, which may be optionally pegylated. In yet a further embodiment, the interferon is interferon alpha (IFN-α), interferon beta (IFN-β), interferon lambda (IFN-λ), or interferon gamma (IFN-γ). In a preferred embodiment, the interferon is interferon-alpha-2a, interferon-alpha-2b, interferon-alpha-n1, pegylated interferon-alpha-2a, or pegylated interferon-alpha-2b.

In any of the methods provided herein, the method may further comprise administering to the individual at least one HBV vaccine, a nucleoside HBV inhibitor, or any combination thereof. In an embodiment, the HBV vaccine is at least one of Recombivax HB, Engerix-B, Elovac B, GeneVac-B, or Shanvac B.

In another embodiment of the methods provided herein, administering the compound of Formula I, II, III, or IV allows for administering of the at least one additional therapeutic agent at a lower dose or frequency as compared to the administering of the at least one additional therapeutic agent alone that is required to achieve similar results in prophylactically treating an HBV infection in an individual in need thereof.

In another embodiment of the methods provided herein, administering the compound of Formula I, II, III, or IV reduces the viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and any combination thereof.

In another embodiment of the methods provided herein, the administering of the compound of Formula I, II, III, or IV causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another aspect, provided herein is method of treating an HBV infection in an individual in need thereof, comprising reducing the HBV viral load by administering to the individual a therapeutically effective amount of a compound of Formula I, II, III, or IV alone or in combination with a reverse transcriptase inhibitor; and further administering to the individual a therapeutically effective amount of HBV vaccine. In an embodiment, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine In another embodiment of the methods provided herein, the method further comprises monitoring the HBV viral load, and wherein the method is carried out for a period of time such that the HBV virus is undetectable.

DETAILED DESCRIPTION OF THE INVENTION

Provided herein are compounds that are useful in the treatment and prevention of HBV in man. In a non-limiting aspect, these compounds modulate and/or disrupt HBV assembly by interacting with HBV capsid to afford defective viral particles with greatly reduced virulence. The compounds of the invention have potent antiviral activity, exhibit favorable metabolic, tissue distribution, safety and pharmaceutical profiles, and are suitable for use in man.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, proper capsid assembly has been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication.

The more conserved a drug target is, the fewer replication-competent resistance mutations are acquired by patients. Indeed, natural mutations in HBV capsid for chronically infected patients accumulate in only four out of 183 residues in the full length protein. Thus, HBV capsid assembly inhibitors may elicit lower drug resistance emergence rates relative to existing HBV antivirals. Further, drug therapy that targets HBV capsid could be less prone to drug-resistant mutations when compared to drugs that target traditional NA enzyme active sites. Reports describing compounds that bind viral capsids and inhibit replication of HIV, rhinovirus and HBV provide strong pharmacological proof of concept for viral capsid proteins as antiviral drug targets.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA.

DEFINITIONS

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "capsid assembly modulator" refers to a compound that disrupts and/or accelerates and/or inhibits and/or hinders and/or delays and or reduces and/or modifies normal capsid assembly (e.g., during maturation) and/or normal capsid disassembly (e.g., during infectivity) and/or perturbs capsid stability, thereby inducing aberrant capsid morphology and function. In one embodiment, a capsid assembly modulator accelerates capsid assembly and/or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly and/or disassembly. In yet another embodiment, a capsid assembly modulator causes a perturbation in structure and/or function of CA (e.g., ability of CA to assemble, disassemble, bind to a substrate, fold into a suitable conformation, or the like), which attenuates viral infectivity and/or is lethal to the virus.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "ddA" refers to 2',3'-dideoxyadenosine.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_{1-6}$)alkyl, particularly ethyl, methyl, isopropyl, isobutyl, n-pentyl, n-hexyl and cyclopropylmethyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_{3-10}$ cycloalkyl), or groups having 3 to 7 ring atoms ($C_{3-7}$ cycloalkyl). Illustrative examples of cycloalkyl groups include, but are not limited to, the following moieties:

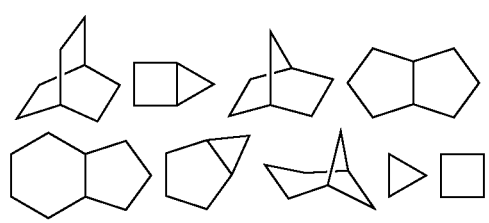

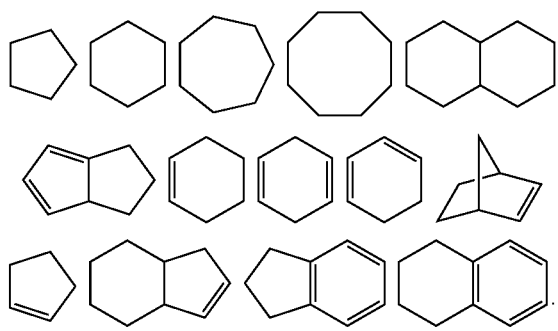

Monocyclic cycloalkyls include, but are not limited to, cyclopropyl, cyclobutyl, cyclopentyl, cyclohexyl, cycloheptyl, and cyclooctyl. Dicyclic cycloalkys include, but are not limited to, tetrahydronaphthyl, indanyl, and tetrahydropentalene. Polycyclic cycloalkys include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

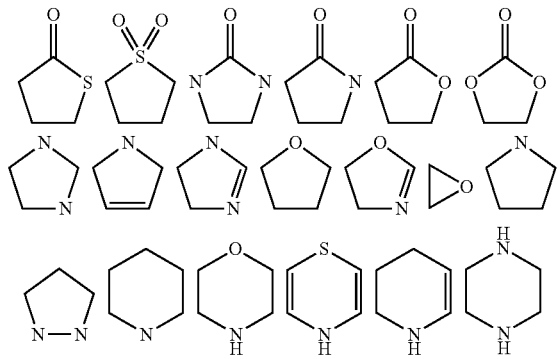

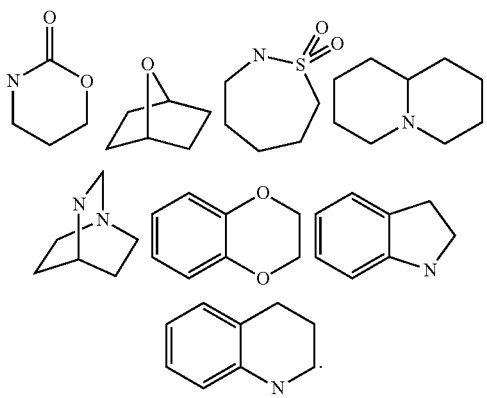

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "heteroaryl" or "heteroaromatic" refers to a heterocycle having aromatic character. A polycyclic heteroaryl may include one or more rings that are partially saturated. Examples include the following moieties:

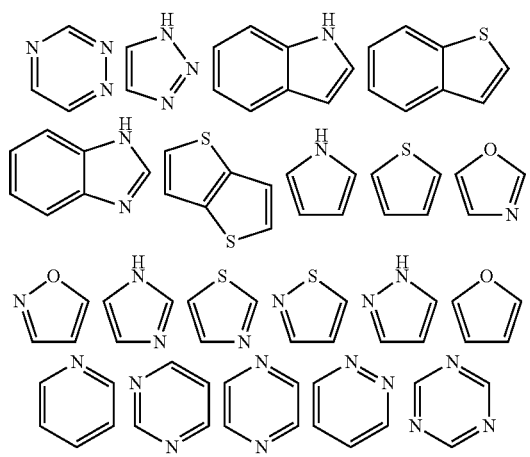

-continued

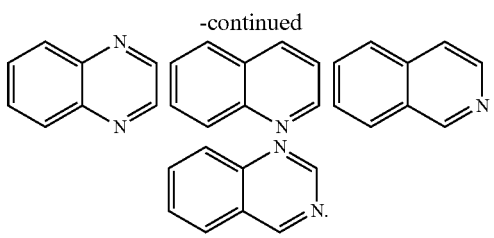

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

It is noted for the generic structures described herein that rings that are substituted by two or more variables (eg., the Cy ring of Formula I) can indicate, for example, either viscinal (e.g., compounds 1735-1737) or geminal (e.g., compounds 1732-1734) substitution patterns.

Compounds of the Invention

The present invention relates to the discovery of compounds that are useful in the treatment and prevention of HBV in man. In one aspect, the compounds of the invention are useful in HBV treatment by disrupting, accelerating, reducing delaying and/or inhibiting normal viral capsid assembly and/or disassembly of immature or mature particles, thereby inducing aberrant capsid morphology and leading to antiviral effects such as disruption of virion assembly and/or disassembly and/or virion maturation, and/or virus egress.

The capsid assembly disruptors disclosed herein may be used as monotherapy and/or in cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV capsid assembly inhibitors of the present invention in combination with, for example, NA drugs, is likely to deliver a more profound antiviral effect and greater disease eradication rates than current standards of care.

Capsid assembly plays a central role in HBV genome replication. HBV polymerase binds pre-genomic HBV RNA (pgRNA), and pgRNA encapsidation must occur prior to HBV DNA synthesis. Moreover, it is well established that nuclear accumulation of the cccDNA replication intermediate, which is responsible for maintenance of chronic HBV replication in the presence of nucleoside suppressive therapy, requires the capsid for shuttling HBV DNA to the nuclei. Therefore, the HBV capsid assembly disruptors of the invention have the potential to increase HBV eradication rates through synergistic or additive suppression of viral genome replication and to further reduce accumulation of cccDNA when used alone or in combination with existing nucleoside drugs. The capsid assembly disruptors of the present invention may also alter normal core protein degradation, potentially leading to altered MHC-1 antigen presentation, which may in turn increase seroconversion/eradication rates through immuno-stimulatory activity, more effectively clearing infected cells.

In one aspect, drug resistance poses a major threat to current therapies for chronic HBV infection, and cross-class combination therapy is a proven strategy for delaying emergence of drug resistance strains. The capsid assembly disruptors of the present invention can, when administered alone or in combination with other HBV therapy, offer enhanced drug resistant profiles and improved management of chronic HBV.

The compounds useful within the invention can be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula I:

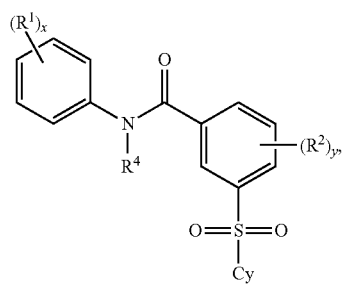

I or a pharmaceutically acceptable salt thereof;
wherein
$R^4$ is H or $C_1$-$C_3$ alkyl;
each $R^1$ is, independently at each occurrence, OH, halo, —CN, —NO$_2$, $R^{11}$, or OR$^{11}$, wherein $R^{11}$ is, independently at each occurrence, —$C_1$-$C_6$ alkyl or —$C_1$-$C_6$ heteroalkyl, wherein the alkyl and heteroalkyl groups are optionally substituted 1-5 times with halo, —OH, —CN, or —NO$_2$;
each $R^2$ is, independently at each occurrence, OH, halo, —CN, —NO$_2$, $R^{12}$, OR$^{12}$, or SR$^{12}$, wherein $R^{12}$ is, independently at each occurrence, —$C_1$-$C_6$ alkyl, or —$C_3$-$C_{10}$ cycloalkyl, wherein the alkyl and cycloalkyl groups are optionally substituted 1-5 times with halo, —OH, —CN, or —$NO_2$;

Cy is

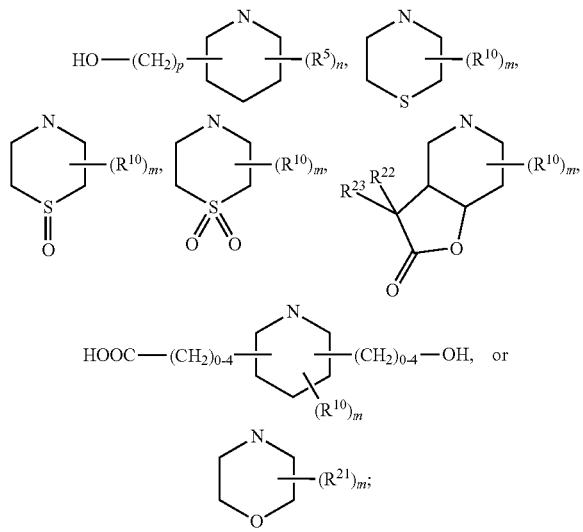

each $R^5$ is, independently at each occurrence, halo, —$C_1$-$C_6$ haloalkyl, or —O—$C_1$-$C_6$ haloalkyl;

each $R^{10}$ is, independently at each occurrence, halo, OH, —$C_1$-$C_6$ alkyl, or —O—$C_1$-$C_6$ alkyl, wherein the alkyl group is optionally substituted 1-3 times with halo or OH;

$R^{22}$ and $R^{23}$ are, independently at each occurrence, H, halo, OH, —$C_1$-$C_6$ alkyl, or —O—$C_1$-$C_6$ alkyl, wherein the alkyl group is optionally substituted 1-3 times with halo or OH;

each $R^{21}$ is, independently at each occurrence, halo, OH, —$C_1$-$C_6$ alkyl, or —$C_1$-$C_6$ alkoxy, wherein the alkyl group is substituted 1-3 times with halo or OH, and the alkoxy group is optionally substituted 1-3 times with halo or OH;

n is 2, 3, or 4;
p is 0, 1, 2, 3, or 4;
m is 0, 1, 2, 3, or 4;
x is 1, 2, 3, 4, or 5; and
y is 1, 2, 3, or 4.

In one embodiment of Formula I provided herein,
$R^4$ is H or $C_1$-$C_3$ alkyl;

each $R^1$ is, independently at each occurrence, OH, halo, $R^{11}$, or $OR^{11}$, wherein $R^{11}$ is, independently at each occurrence, —$C_1$-$C_6$ alkyl or —$C_1$-$C_6$ heteroalkyl, wherein the alkyl and heteroalkyl groups are optionally substituted 1-5 times with halo or —OH;

each $R^2$ is, independently at each occurrence, OH, halo, $R^{12}$, $OR^{12}$, or $SR^{12}$, wherein $R^{12}$ is, independently at each occurrence, —$C_1$-$C_6$ alkyl or —$C_3$-$C_{10}$ cycloalkyl, wherein the alkyl and cycloalkyl groups are optionally substituted 1-5 times with halo or —OH;

Cy is

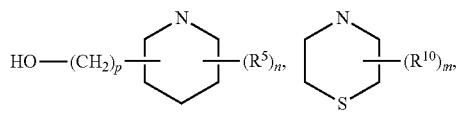

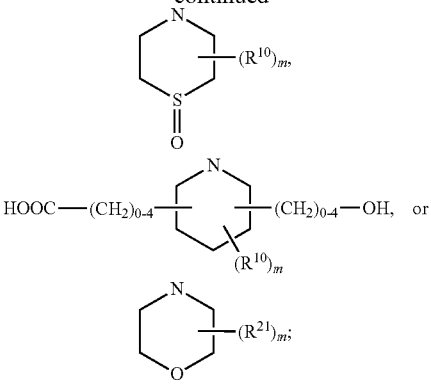

each $R^5$ is, independently at each occurrence, halo;

each $R^{10}$ is, independently at each occurrence, halo, OH, —$C_1$-$C_6$ alkyl, or —O—$C_1$-$C_6$ alkyl, wherein the alkyl group is optionally substituted 1-3 times with halo or OH;

each $R^{21}$ is, independently at each occurrence, halo, OH, —$C_1$-$C_6$ alkyl, or —$C_1$-$C_6$ alkoxy, wherein the alkyl group is substituted 1-3 times with halo or OH, and the alkoxy group is optionally substituted 1-3 times with halo or OH;

n is 2, 3, or 4;
p is 0, 1, 2, 3, or 4;
m is 0, 1, 2, 3, or 4;
x is 1, 2, or 3; and
y is 1, 2, or 3.

In another embodiment of Formula I provided herein,
$R^4$ is H or $C_1$-$C_3$ alkyl;

each $R^1$ is, independently at each occurrence, OH, halo, —$C_1$-$C_6$ alkyl, or —O—$C_1$-$C_6$ alkyl, wherein the alkyl group is optionally substituted 1-5 times with OH or halo;

each $R^2$ is, independently at each occurrence, OH, halo, $R^{12}$, or $OR^{12}$, wherein $R^{12}$ is, independently at each occurrence, —$C_1$-$C_6$ alkyl or —$C_3$-$C_{10}$ cycloalkyl, wherein the alkyl and cycloalkyl groups are optionally substituted 1-5 times with halo or —OH;

Cy is

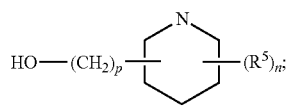

each $R^5$ is, independently at each occurrence, halo;

n is 2, 3, or 4;
p is 0, 1, 2, or 3;
x is 1, 2, or 3; and
y is 1, 2, or 3.

In one embodiment of Formula I provided herein, $R^4$ is H.

In another embodiment of Formula I provided herein, each $R^1$ is, independently at each occurrence, halo, and x is 1, 2, or 3.

In another embodiment of Formula I provided herein, the compound is of the Formula II:

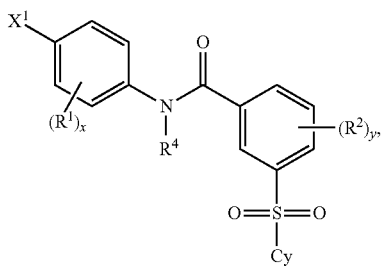

or a pharmaceutically acceptable salt thereof, wherein $X^1$ is halo.

In another embodiment of Formula I and Formula II provided herein, each $R^2$ is, independently at each occurrence, OH, halo, —$C_1$-$C_6$ alkyl, —$C_1$-$C_6$ alkyl substituted 1-3 times with halo, —O—$C_1$-$C_6$ alkyl, or —O—$C_3$-$C_{10}$ cycloalkyl.

In another embodiment of Formula I and Formula II provided herein, $R^2$ is —S—$C_1$-$C_6$ alkyl, and y is 1.

In another embodiment of Formula I and Formula II provided herein, $R^2$ is halo, —$C_1$-$C_6$ alkyl, or —$C_1$-$C_6$ alkyl substituted 1-3 times with halo, and y is 1.

In another embodiment of Formula I and Formula II provided herein, $R^2$ is OH, —$OCH_3$, —$OCH_2CH_3$, —$OCH_2CH_2CH_3$, or —O-cyclopropyl, and y is 1.

In another embodiment of Formula I and Formula II provided herein, $R^2$ is —$SCH_3$, and y is 1.

In another embodiment of Formula I and Formula II provided herein, y is 0.

In a further embodiment of Formula I and Formula II provided herein, the compound is of Formula III:

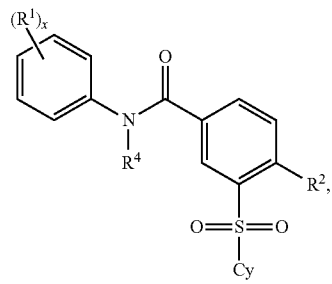

or a pharmaceutically acceptable salt thereof.

In another embodiment of Formula I and Formula II provided herein, the compound is of Formula IIIa:

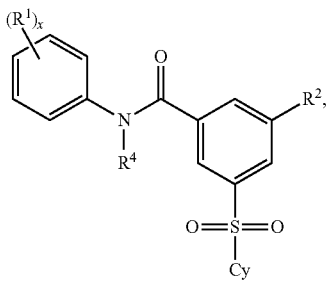

or a pharmaceutically acceptable salt thereof.

In still another embodiment of Formulas I-III and IIIa provided herein, Cy is

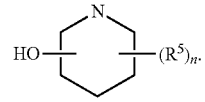

In another embodiment of Formulas I-III and IIIa provided herein, Cy is

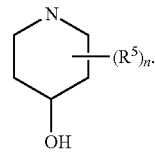

In another embodiment of Formulas I-III and IIIa provided herein, Cy is

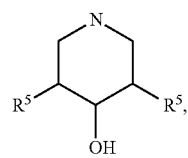

and each $R^5$ is, independently at each occurrence, halo.

In a further embodiment of Formulas I-III and IIIa provided herein, Cy is

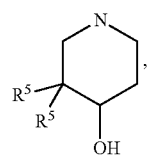

and each $R^5$ is, independently at each occurrence, halo.

In another aspect, provided herein is a compound of Formula IV:

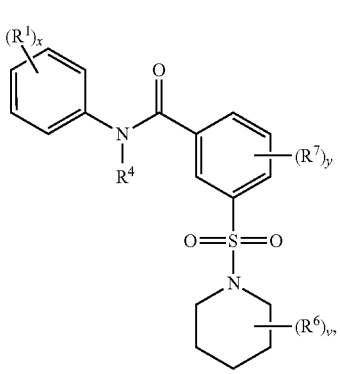

or a pharmaceutically acceptable salt thereof;
wherein
$R^4$ is H or $C_1$-$C_3$ alkyl;
each $R^1$ is, independently at each occurrence, OH, halo, —CN, —$NO_2$, $R^{11}$, or $OR^{11}$, wherein $R^{11}$ is, independently at each occurrence, —$C_1$-$C_6$ alkyl or —$C_1$-$C_6$ heteroalkyl, wherein the alkyl and heteroalkyl groups are optionally substituted 1-5 times with halo, —OH, —CN, or —$NO_2$;

each $R^7$ is, independently at each occurrence, —$C_1$-$C_6$ haloalkyl, —O—$C_1$-$C_6$ alkyl, or —O—$C_3$-$C_{10}$ cycloalkyl, wherein the alkyl and cycloalkyl groups are optionally substituted 1-5 times with halo;

each $R^6$ is, independently at each occurrence, OH, halo, —CN, —$NO_2$, $R^{16}$, or $OR^{16}$, wherein $R^{16}$ is, independently at each occurrence, —$C_1$-$C_6$ alkyl or —$C_1$-$C_6$ heteroalkyl, wherein the alkyl and heteroalkyl groups are optionally substituted 1-5 times with halo, —OH, —CN, or —$NO_2$;

v is 0, 1, or 2;

x is 1, 2, 3, 4, or 5; and y is 1, 2, 3, or 4.

In one embodiment of Formula IV provided herein, $R^4$ is H or $C_1$-$C_3$ alkyl;

each $R^1$ is, independently at each occurrence, OH, halo, $R^{11}$, or $OR^{11}$, wherein $R^{11}$ is, independently at each occurrence, —$C_1$-$C_6$ alkyl or —$C_1$-$C_6$ heteroalkyl, wherein the alkyl and heteroalkyl groups are optionally substituted 1-5 times with halo or —OH;

each $R^7$ is, independently at each occurrence, —$C_1$-$C_6$ haloalkyl, —O—$C_1$-$C_6$ alkyl, or —O—$C_3$-$C_{10}$ cycloalkyl, wherein the alkyl and cycloalkyl groups are optionally substituted 1-5 times with halo;

each $R^6$ is, independently at each occurrence, OH, halo, $R^{16}$, or $OR^{16}$, wherein $R^{16}$ is, independently at each occurrence, —$C_1$-$C_6$ alkyl or —$C_1$-$C_6$ heteroalkyl, wherein the alkyl and heteroalkyl groups are optionally substituted 1-5 times with halo or —OH;

v is 1 or 2;

x is 1, 2, 3, or 4; and y is 1, 2, or 3.

In another embodiment of Formula IV provided herein, $R^4$ is H or $C_1$-$C_3$ alkyl;

each $R^1$ is, independently at each occurrence, OH, halo, —$C_1$-$C_6$ alkyl, or —O—$C_1$-$C_6$ alkyl, wherein the alkyl group is optionally substituted 1-5 times with OH or halo;

each $R^7$ is, independently at each occurrence, —$C_1$-$C_6$ haloalkyl, —O—$C_1$-$C_6$ alkyl, or —O—$C_3$-$C_{10}$ cycloalkyl, wherein the alkyl and cycloalkyl groups are optionally substituted 1-3 times with halo;

each $R^6$ is, independently at each occurrence, OH, halo, —$C_1$-$C_6$ alkyl, or —O—$C_1$-$C_6$ alkyl, wherein the alkyl group is optionally substituted 1-5 times with halo or —OH;

v is 1 or 2;

x is 1, 2, 3, or 4; and y is 1, 2, or 3.

In another embodiment of Formula IV provided herein, $R^4$ is H.

In another embodiment of Formula IV provided herein, each $R^1$ is, independently at each occurrence, halo, and x is 1, 2, or 3.

In another embodiment of Formula IV provided herein, $R^7$ is —$C_1$-$C_6$ haloalkyl, —O—$C_1$-$C_6$ alkyl, or —O—$C_3$-$C_{10}$ cycloalkyl.

In still another embodiment of Formula IV provided herein, $R^7$ is —$C_1$-$C_6$ haloalkyl, and y is 1.

In a further embodiment of Formula IV provided herein, $R^6$ is OH, and v is 1.

Certain embodiments of Formulas I-IV, including pharmaceutically acceptable salts thereof, are shown below in Table 1. All compounds of Formulas I, II, III, IIIa, and IV as well as pharmaceutically acceptable salts thereof, and the compounds of Table 1, as well as pharmaceutically acceptable salts thereof, are considered to be "compounds of the invention."

Synthetic method codes refer to the synthesis methodologies provided in the experimental section.

TABLE 1

| Structure | Compound ID | $^1$H NMR | MS(M + H)$^+$ |
|---|---|---|---|
| 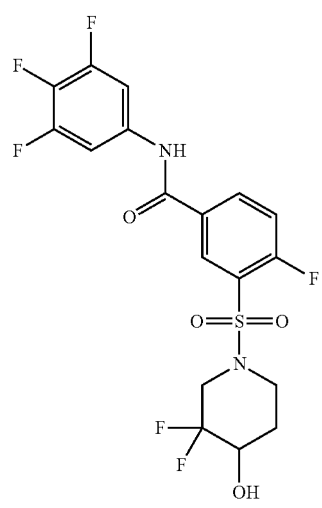 [SMILES: O=C(Nc1cc(F)c(F)c(F)c1)c1ccc(F)c(S(=O)(=O)N2CCC(O)C(F)(F)C2)c1] | 1732 | | 469 |

TABLE 1-continued

| Structure | Compound ID | ¹H NMR | MS(M + H)⁺ |
|---|---|---|---|
| (structure) | 1733 | | 451 |
| (structure) | 1734 | ¹H NMR (400 MHz, CD₃OD) δ 8.49-8.41 (m, 1 H), 8.32-8.24 (m, 1 H), 8.01-7.95 (m, 1 H), 7.68-7.60 (m, 1 H), 7.58-7.48 (m, 1 H), 7.31-7.22 (m, 1 H), 3.98-3.83 (m, 1 H), 3.70-3.55 (m, 2 H), 3.48-3.36 (m, 2 H), 2.06-1.81 (m, 2 H). | 467/469 |
| (structure) | 1962 | ¹H NMR (400 MHz, CD₃OD) δ 8.37 (s, 1 H), 8.26 (d, J = 7.8 Hz, 1 H), 7.98-8.07 (m, 2 H), 7.81 (t, J = 7.8 Hz, 1 H), 7.63-7.69 (m, 1 H), 7.28 (t, J = 9.0 Hz, 1 H), 3.78-3.87 (m, 1 H), 3.37-3.55 (m, 2 H), 3.28 (d, J = 5.8 Hz, 1 H), 3.14-3.23 (m, 1 H), 1.97 (ddd, J = 3.9, 9.0, 13.2 Hz, 1 H), 1.84 (ddd, J = 3.3, 6.7, 13.4 Hz, 1 H). | 449/451 |

TABLE 1-continued

| Structure | Compound ID | $^1$H NMR | MS(M + H)$^+$ |
|---|---|---|---|
| 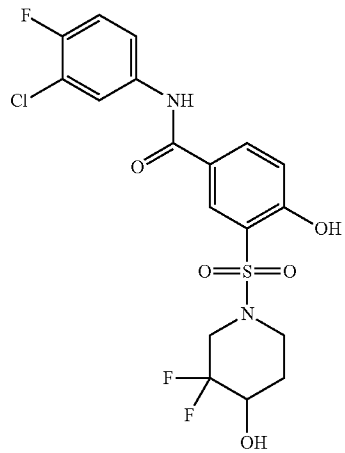 [SMILES: O=C(Nc1ccc(F)c(Cl)c1)c1ccc(O)c(S(=O)(=O)N2CCC(O)C(F)(F)C2)c1] | 1963 | $^1$H NMR (400 MHz, CD$_3$OD) δ 8.47-8.35 (m, 1 H), 8.09-8.04 (m, 1 H), 7.99-7.92 (m, 1 H), 7.64-7.58 (m, 1 H), 7.29-7.22 (m, 1 H), 7.13-7.06 (m, 1 H), 3.96-3.83 (m, 1 H), 3.76-3.54 (m, 2 H), 3.40-3.34 (m, 2 H), 2.08-1.79 (m, 2 H). | 465/467 |
| 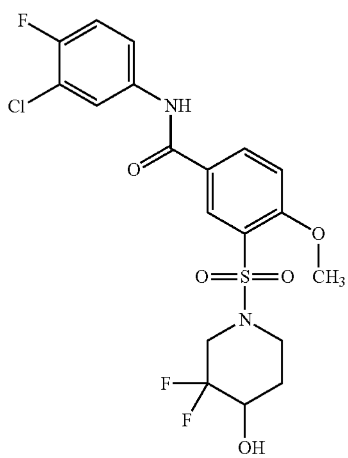 [SMILES: COc1ccc(C(=O)Nc2ccc(F)c(Cl)c2)cc1S(=O)(=O)N1CCC(O)C(F)(F)C1] | 1964 | $^1$H NMR (400 MHz, CD$_3$OD) δ 8.49-8.45 (m, 1 H), 8.26-8.20 (m, 1 H), 8.01-7.94 (m, 1 H), 7.66-7.59 (m, 1 H), 7.40-7.34 (m, 1 H), 7.30-7.22 (m, 1 H), 4.11-4.04 (m, 4 H), 3.95-3.84 (m, 1 H), 3.67-3.56 (m, 2 H), 3.37-3.35 (m, 2 H), 2.09-1.78 (m, 2 H). | 479/481 |
| 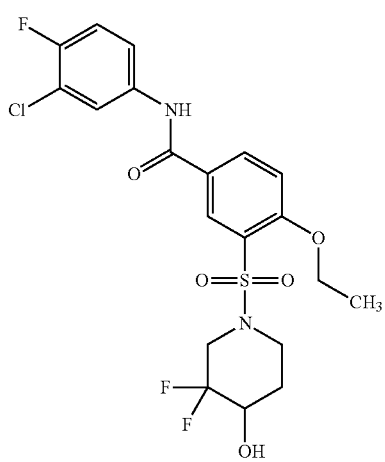 [SMILES: CCOc1ccc(C(=O)Nc2ccc(F)c(Cl)c2)cc1S(=O)(=O)N1CCC(O)C(F)(F)C1] | 1965 | $^1$H NMR (400 MHz, CD$_3$OD) δ 8.50-8.44 (m, 1 H), 8.25-8.15 (m, 1 H), 8.01-7.94 (m, 1 H), 7.68-7.58 (m, 1 H), 7.39-7.21 (m, 2 H), 4.43-4.27 (m, 2 H), 4.00-3.82 (m, 1 H), 3.78-3.54 (m, 2 H), 3.40-3.35 (m, 2 H), 2.05-1.75 (m, 2 H), 1.61-1.46 (m, 3 H). | 493/495 |

TABLE 1-continued
| Structure | Compound ID | ¹H NMR | MS(M + H)⁺ |
|---|---|---|---|
| 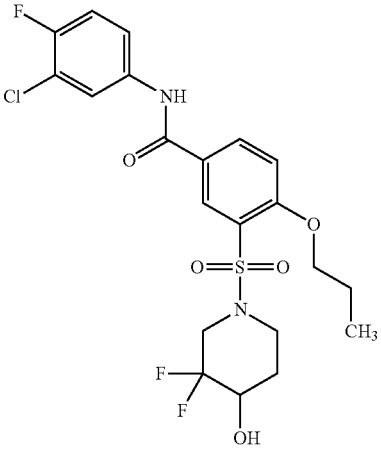 [SMILES: CCCOc1ccc(C(=O)Nc2ccc(F)c(Cl)c2)cc1S(=O)(=O)N1CCC(O)C(F)(F)C1] | 1966 | | 507/509 |
| 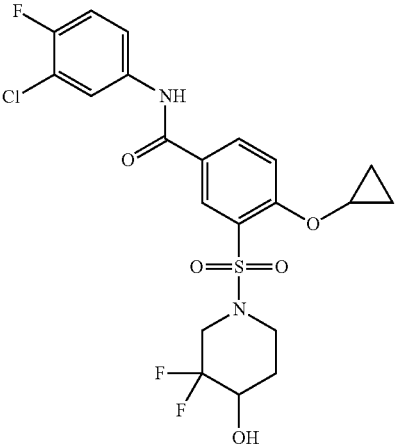 [SMILES: O=C(Nc1ccc(F)c(Cl)c1)c1ccc(OC2CC2)c(S(=O)(=O)N2CCC(O)C(F)(F)C2)c1] | 1967 | ¹H NMR (400 MHz, CD₃OD) δ 8.48-8.44 (m, 1 H), 8.27-8.21 (m, 1 H), 8.00-7.95 (m, 1 H), 7.72-7.67 (m, 1 H), 7.66-7.60 (m, 1 H), 7.29-7.23 (m, 1 H), 4.14-4.04 (m, 1 H), 3.96-3.84 (m, 1 H), 3.70-3.51 (m, 2 H), 3.41-3.34 (m, 2 H), 2.05-1.78 (m, 2 H), 1.01-0.86 (m, 4 H). | 505/507 |
| 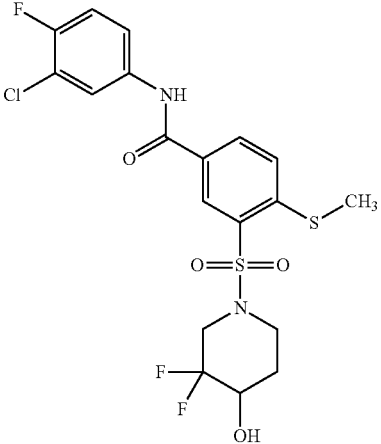 [SMILES: CSc1ccc(C(=O)Nc2ccc(F)c(Cl)c2)cc1S(=O)(=O)N1CCC(O)C(F)(F)C1] | 1968 | ¹H NMR (400 MHz, CD₃OD) δ 8.52-8.48 (m, 1 H), 8.16-8.10 (m, 1 H), 8.01-7.95 (m, 1 H), 7.67-7.59 (m, 2 H), 7.31-7.22 (m, 1 H), 3.95-3.84 (m, 1 H), 3.76-3.58 (m, 2 H), 3.45-3.35 (m, 2 H), 2.63 (s, 3 H), 2.06-1.81 (m, 2 H). | 495/497 |

TABLE 1-continued
| Structure | Compound ID | ¹H NMR | MS(M + H)⁺ |
|---|---|---|---|
| 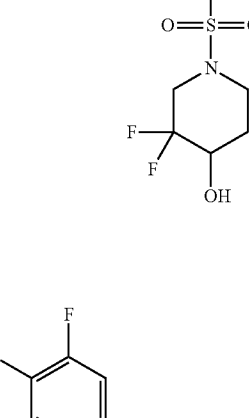 | 1969 | ¹H NMR (400 MHz, CD₃OD) δ 8.49 (d, J = 1.9, Hz, 1 H), 8.14-8.08 (m, 1 H), 8.02-7.96 (m, 1 H), 7.67-7.57 (m, 2 H), 7.31-7.24 (m, 1 H), 3.96-3.87 (m, 1 H), 3.70-3.50 (m, 2 H), 3.40-3.35 (m, 1 H), 3.31-3.24 (m, 1 H), 2.70 (s, 3 H), 2.05-1.93 (m, 1 H), 1.89-1.79 (m, 1 H). | 463/465 |
| 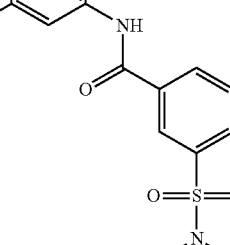 | 1993 | | 483 |
| 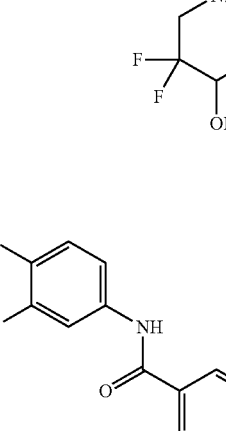 | 1994 | | 465 |

TABLE 1-continued

| Structure | Compound ID | ¹H NMR | MS(M + H)⁺ |
|---|---|---|---|
| 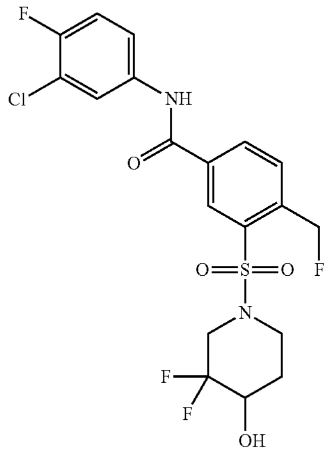 [SMILES: O=C(Nc1ccc(F)c(Cl)c1)c1ccc(CF)c(S(=O)(=O)N2CCC(O)C(F)(F)C2)c1] | 1995 | | 481/483 |
| 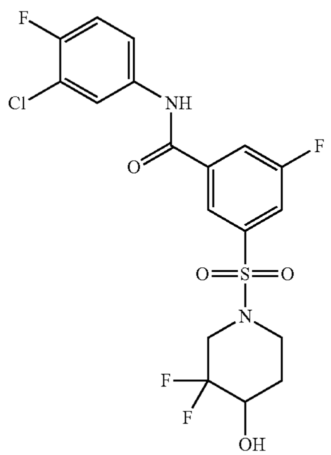 [SMILES: O=C(Nc1ccc(F)c(Cl)c1)c1cc(F)cc(S(=O)(=O)N2CCC(O)C(F)(F)C2)c1] | 2051 | ¹H NMR (400 MHz, CD₃OD) δ 8.22 (s, 1 H), 8.08-8.03 (m, 1 H), 8.00 (dd, J = 2.6, 6.7 Hz, 1 H), 7.84 (td, J = 1.9, 7.7 Hz, 1 H), 7.66 (ddd, J = 2.7, 4.1, 9.0 Hz, 1 H), 7.28 (t, J = 9.0 Hz, 1 H), 3.90-3.81 (m, 1 H), 3.59-3.40 (m, 2 H), 3.32-3.29 (m, 1 H), 3.29-3.20 (m, 1 H), 1.98 (ddd, J = 4.4, 8.8, 13.3 Hz, 1 H), 1.84 (tdd, J = 3.4, 6.8, 10.3 Hz, 1 H). | 467/469 |
| 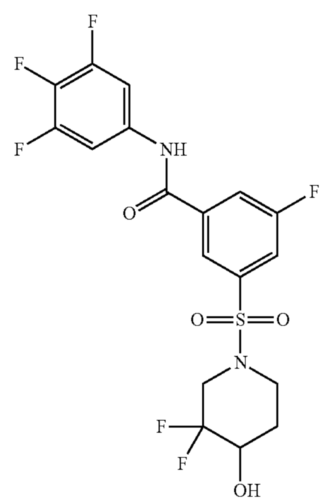 [SMILES: O=C(Nc1cc(F)c(F)c(F)c1)c1cc(F)cc(S(=O)(=O)N2CCC(O)C(F)(F)C2)c1] | 2059 | ¹H NMR (400 MHz, CD₃OD) δ 8.22 (s, 1 H), 8.05 (d, J = 8.5 Hz, 1 H), 7.87-7.82 (m, 1 H), 7.63 (dd, J = 6.4, 9.9 Hz, 2 H), 3.90-3.80 (m, 1 H), 3.60-3.39 (m, 2 H), 3.31-3.19 (m, 2 H), 1.97 (ddd, J = 4.4, 9.0, 13.4 Hz, 1 H), 1.84 (tdd, J = 3.2, 6.8, 10.2 Hz, 1 H). | 469 |

TABLE 1-continued

| Structure | Compound ID | ¹H NMR | MS(M + H)⁺ |
|---|---|---|---|
| 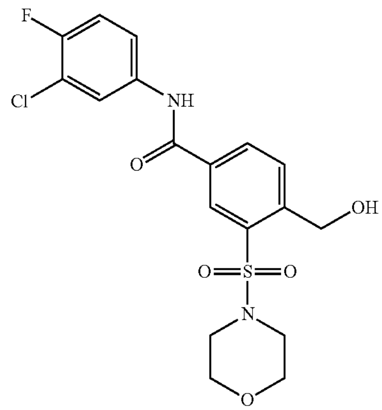 [SMILES: O=C(Nc1ccc(F)c(Cl)c1)c1ccc(CO)c(S(=O)(=O)N2CCOCC2)c1] | 1781 | | |
| 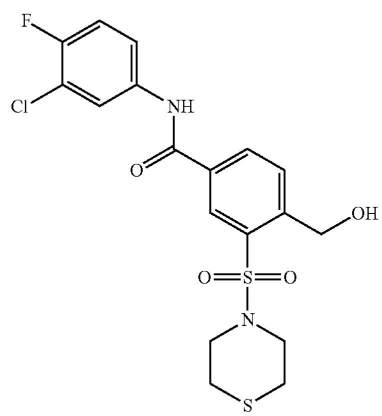 [SMILES: O=C(Nc1ccc(F)c(Cl)c1)c1ccc(CO)c(S(=O)(=O)N2CCSCC2)c1] | 1782 | | |
| 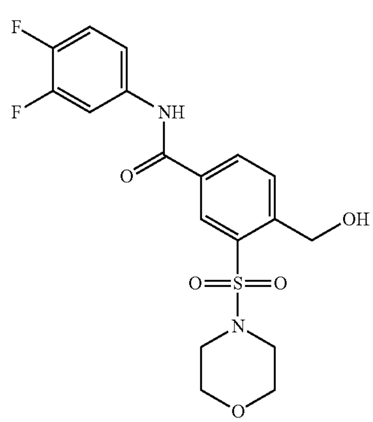 [SMILES: O=C(Nc1ccc(F)c(F)c1)c1ccc(CO)c(S(=O)(=O)N2CCOCC2)c1] | 1788 | | |

TABLE 1-continued

| Structure | Compound ID | ¹H NMR | MS(M + H)⁺ |
|---|---|---|---|
| 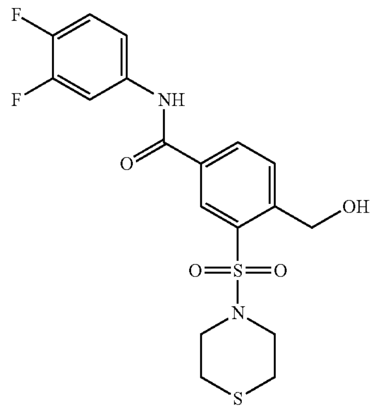 | 1789 | | |
| 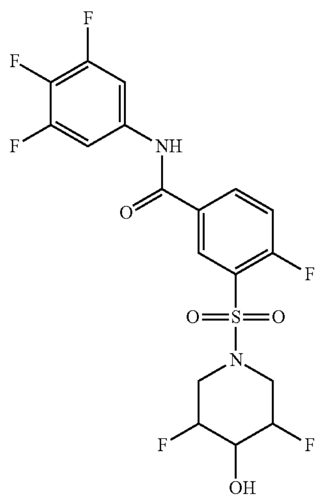 [SMILES: O=C(Nc1cc(F)c(F)c(F)c1)c1ccc(F)c(S(=O)(=O)N2CC(F)C(O)C(F)C2)c1] | 1735 | | |
| 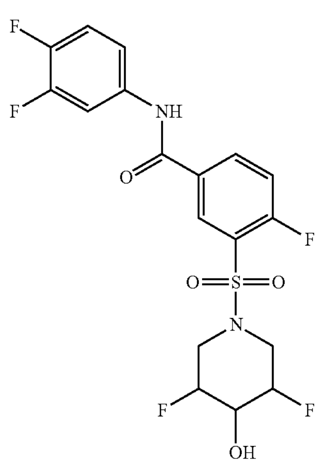 [SMILES: O=C(Nc1ccc(F)c(F)c1)c1ccc(F)c(S(=O)(=O)N2CC(F)C(O)C(F)C2)c1] | 1736 | | |

TABLE 1-continued

| Structure | Compound ID | ¹H NMR | MS(M + H)⁺ |
|---|---|---|---|
| 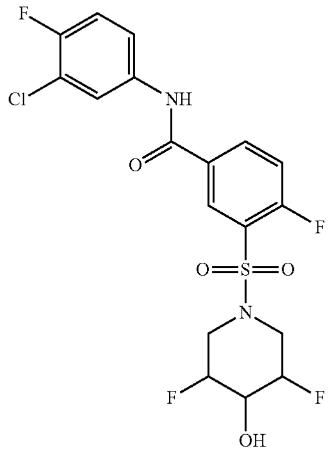 [SMILES: O=C(Nc1ccc(F)c(Cl)c1)c1ccc(F)c(S(=O)(=O)N2CC(F)C(O)C(F)C2)c1] | 1737 | | |
| 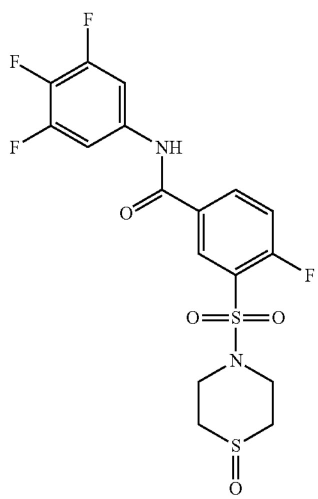 [SMILES: O=C(Nc1cc(F)c(F)c(F)c1)c1ccc(F)c(S(=O)(=O)N2CCS(=O)CC2)c1] | 1738 | | |
| 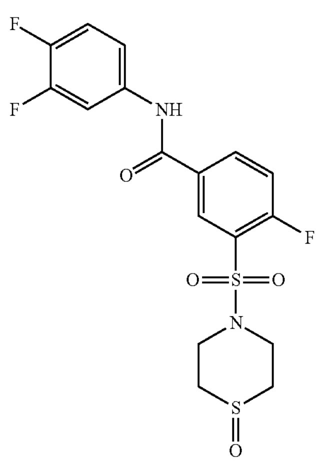 [SMILES: O=C(Nc1ccc(F)c(F)c1)c1ccc(F)c(S(=O)(=O)N2CCS(=O)CC2)c1] | 1739 | | |

TABLE 1-continued
| Structure | Compound ID | ¹H NMR | MS(M + H)⁺ |
|---|---|---|---|
| 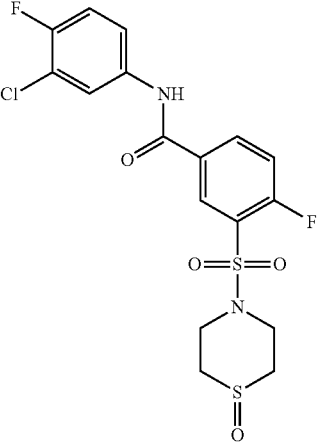 [SMILES: O=C(Nc1ccc(F)c(Cl)c1)c1ccc(F)c(S(=O)(=O)N2CCS(=O)CC2)c1] | 1740 | | |
| 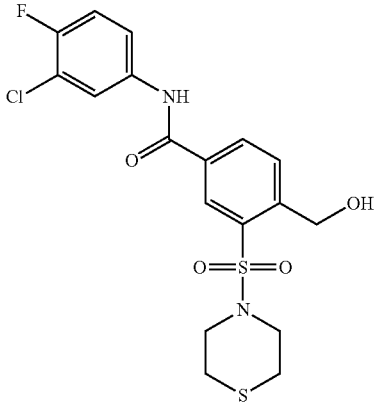 [SMILES: O=C(Nc1ccc(F)c(Cl)c1)c1ccc(CO)c(S(=O)(=O)N2CCSCC2)c1] | 1782 | | |
| 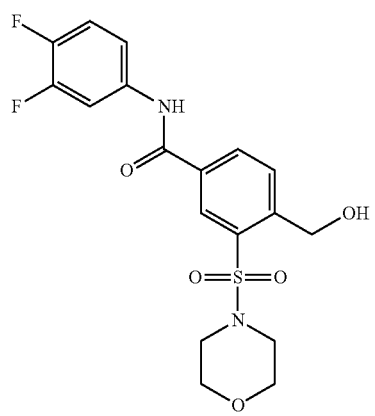 [SMILES: O=C(Nc1ccc(F)c(F)c1)c1ccc(CO)c(S(=O)(=O)N2CCOCC2)c1] | 1788 | | |

TABLE 1-continued

| Structure | Compound ID | ¹H NMR | MS(M + H)⁺ |
|---|---|---|---|
| 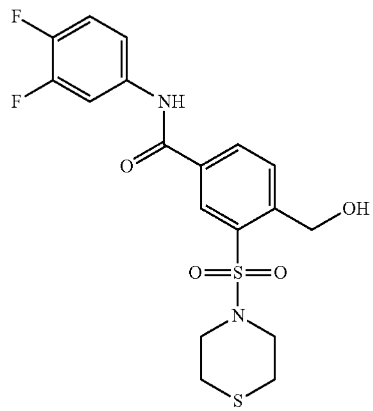 | 1789 | | |
| 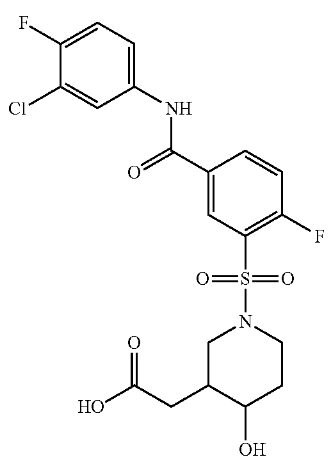 [SMILES: O=C(O)CC1CN(S(=O)(=O)c2cc(C(=O)Nc3ccc(F)c(Cl)c3)ccc2F)CCC1O] | 1905 | | |
| 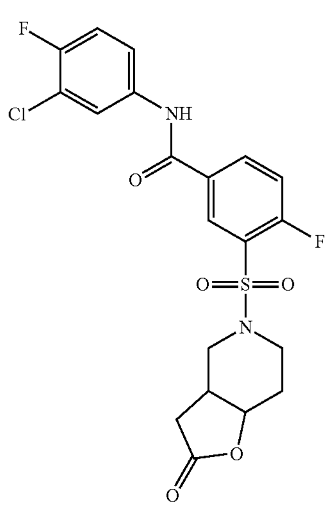 [SMILES: O=C1CC2CN(S(=O)(=O)c3cc(C(=O)Nc4ccc(F)c(Cl)c4)ccc3F)CCC2O1] | 1906 | | |

TABLE 1-continued

| Structure | Compound ID | ¹H NMR | MS(M + H)⁺ |
|---|---|---|---|
| 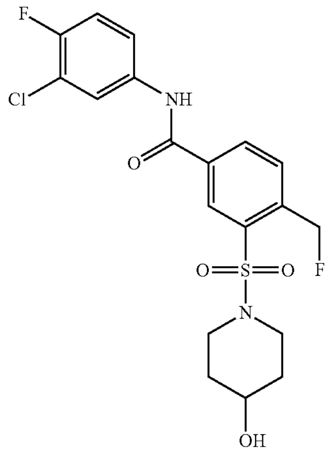 [SMILES: O=C(Nc1ccc(F)c(Cl)c1)c1ccc(CF)c(S(=O)(=O)N2CCC(O)CC2)c1] | 1948 | | |
| 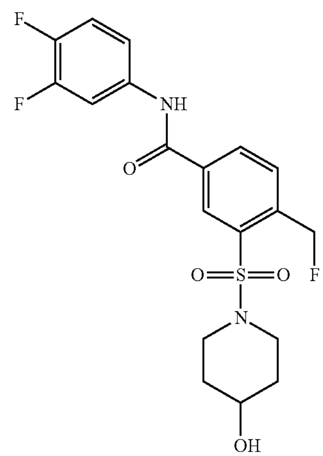 [SMILES: O=C(Nc1ccc(F)c(F)c1)c1ccc(CF)c(S(=O)(=O)N2CCC(O)CC2)c1] | 1949 | | |
| 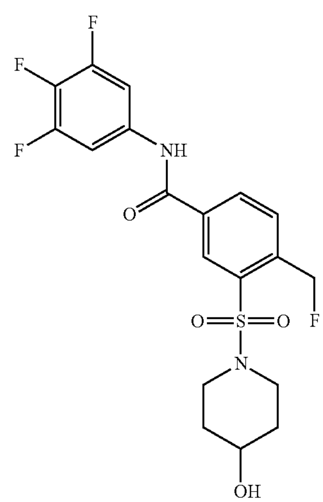 [SMILES: O=C(Nc1cc(F)c(F)c(F)c1)c1ccc(CF)c(S(=O)(=O)N2CCC(O)CC2)c1] | 926 | | |

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral center. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

Methods of the Invention

The invention provides a method of treating an HBV infection in an individual in need thereof, comprising administering to the individual a therapeutically effective amount of a compound of the invention.

The invention also provides a method of eradicating an HBV infection in an individual in need thereof, comprising administering to the individual a therapeutically effective amount of a compound of the invention.

The invention also provides a method of reducing viral load associated with an HBV infection in an individual in need thereof, comprising administering to the individual a therapeutically effective amount of a compound of the invention.

The invention further provides a method of reducing reoccurrence of an HBV infection in an individual in need thereof, comprising administering to the individual a therapeutically effective amount of a compound of the invention.

The invention also provides a method of reducing an adverse physiological impact of an HBV infection in an individual in need thereof, comprising administering to the individual a therapeutically effective amount of a compound of the invention.

The invention further provides a method of reducing, slowing, or inhibiting an HBV infection in an individual in need thereof, comprising administering to the individual a therapeutically effective amount of a compound of the invention.

The invention also provides a method of inducing remission of hepatic injury from an HBV infection in an individual in need thereof, comprising administering to the individual a therapeutically effective amount of a compound of the invention.

The invention further provides a method of reducing the physiological impact of long-term antiviral therapy for HBV infection in an individual in need thereof, comprising administering to the individual a therapeutically effective amount of a compound of the invention.

The invention further provides a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms. In another embodiment, the compound of the invention and the at least one additional therapeutic agent are co-formulated. In yet another embodiment, the compound of the invention and the at least one additional therapeutic agent are co-administered.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the method of the invention reduces viral load in an individual suffering from an HBV infection to a greater extent compared to the extent that other therapeutic classes of HBV drugs reduce viral load in the individual.

In one embodiment, the administering of a compound of the invention, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a compound of the invention, or a pharmaceutically acceptable salt thereof, reduces the viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and any combination thereof.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

In another embodiment, the method of the invention further comprises monitoring the HBV viral load of the subject, and wherein the method is carried out for a period of time such that the HBV virus is undetectable.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Formula II, or a pharmaceutically acceptable salt thereof.

In another embodiment, provided herein is a method of treating an HBV infection in an individual in need thereof, comprising administering to the individual a therapeutically effective amount of a compound of Formula III, or a pharmaceutically acceptable salt thereof.

In another embodiment, provided herein is a method of treating an HBV infection in an individual in need thereof, comprising administering to the individual a therapeutically effective amount of a compound of Formula IIIa, or a pharmaceutically acceptable salt thereof.

In another embodiment, provided herein is a method of treating an HBV infection in an individual in need thereof, comprising administering to the individual a therapeutically effective amount of a compound of Formula IV, or a pharmaceutically acceptable salt thereof.

In another embodiment, provided herein is a method of treating an HBV infection in an individual in need thereof, comprising administering to the individual a therapeutically effective amount of compound 1732, or a pharmaceutically acceptable salt thereof.

In another embodiment, provided herein is a method of treating an HBV infection in an individual in need thereof, comprising administering to the individual a therapeutically effective amount of compound 1733, or a pharmaceutically acceptable salt thereof.

In another embodiment, provided herein is a method of treating an HBV infection in an individual in need thereof, comprising administering to the individual a therapeutically effective amount of compound 1734, or a pharmaceutically acceptable salt thereof.

In another embodiment, provided herein is a method of treating an HBV infection in an individual in need thereof, comprising administering to the individual a therapeutically effective amount of compound 1963, or a pharmaceutically acceptable salt thereof.

In another embodiment, provided herein is a method of treating an HBV infection in an individual in need thereof, comprising administering to the individual a therapeutically effective amount of compound 1964, or a pharmaceutically acceptable salt thereof.

In another embodiment, provided herein is a method of treating an HBV infection in an individual in need thereof, comprising administering to the individual a therapeutically effective amount of compound 1965, or a pharmaceutically acceptable salt thereof.

In another embodiment, provided herein is a method of treating an HBV infection in an individual in need thereof, comprising administering to the individual a therapeutically effective amount of compound 1967, or a pharmaceutically acceptable salt thereof.

In another embodiment, provided herein is a method of treating an HBV infection in an individual in need thereof, comprising administering to the individual a therapeutically effective amount of compound 1995, or a pharmaceutically acceptable salt thereof.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, reverse transcriptase inhibitor, a TLR-agonist, and other agents with distinct or unknown mechanisms that affect the HBV life cycle and/or affect the consequences of HBV infection.

In non-limiting examples, the compounds of the invention may be used in combination with one or more drugs (or a salt thereof) selected from the group consisting of:

HBV reverse transcriptase inhibitors, and DNA and RNA polymerase inhibitors, including but not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as, but not limited to BAY 41-4109;

reverse transcriptase inhibitor;

a TLR-agonist; and agents of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member the family of highly homologous species-specific proteins that inhibit viral replication and cellular proliferation, and modulate immune response. Human interferons are grouped into three classes; Type I, which include interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons include pegylated interferons and glycosylated interferons. Examples of interferons include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferson alpha-2b.

Accordingly, in one embodiment, the compounds of Formulas I, II, III, IIIa, or IV can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor and/or DNA and/or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In one embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxyethoxy)adenine) and AZD 8848 (methyl[3-({[3-(6-amino-2-butoxy-8-oxo-7,8-dihydro-9H-purin-9-yl)propyl][3-(4-morpholinyl)propyl]amino}methyl)phenyl]acetate).

In any of the methods provided herein, the method may further comprise administering to the individual at least one HBV vaccine, a nucleoside HBV inhibitor, an interferon or any combination thereof. In an embodiment, the HBV vaccine is at least one of Recombivax HB, Engerix-B, Elovac B, GeneVac-B, or Shanvac B.

In another aspect, provided herein is method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine. The reverse transcriptase inhibitor may be one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

In another aspect, provided herein is a pharmaceutical composition comprising a compound of the invention, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragées, liquids, drops, suppositories, or capsules, caplets and gelcaps. The compositions intended for oral use may be prepared according to any method known in the art and such compositions may contain one or more agents selected from the group consisting of inert, non-toxic pharmaceutical excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

1 Procedure for Preparation of Compounds 1732-1734

1.1 General Scheme:

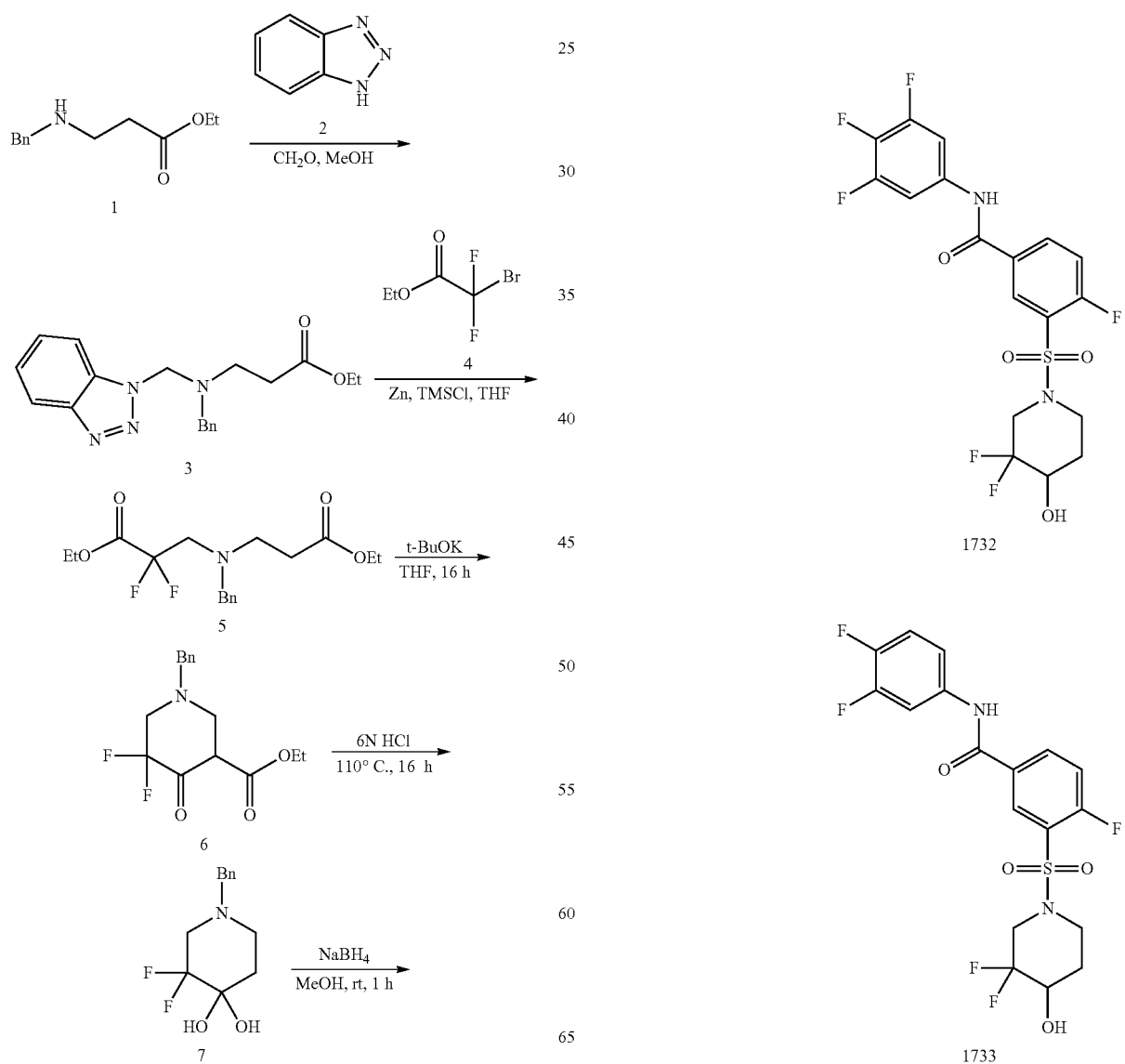

-continued

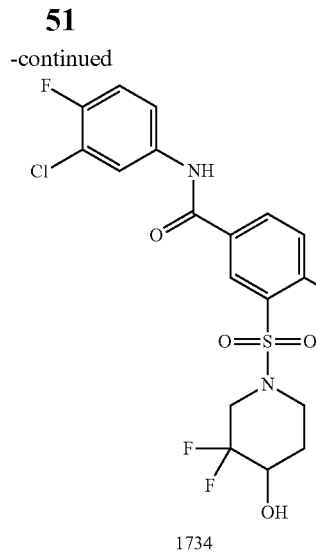

1734

1.1.1 Preparation of Compound 3

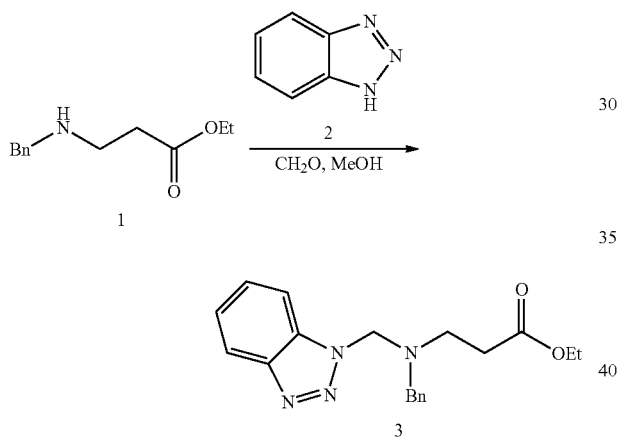

To a solution of compound 1 (10.0 g, 45.8 mmol) in MeOH (32 mL) at 0° C. was added compound 2 (5.46 g, 45.8 mmol) and aqueous HCHO solution (4.56 mL, 59.6 mmol, 40%), then the reaction mixture was stirred at rt for 16 h. The mixture was concentrated in vacuum to give the crude product which was purified by column chromatography on silica gel column (PE:EA=1:1) to give compound 3 (12.5 g, yield 77%). LCMS: 339 [M+1].

1.1.2 Preparation of Compound 5

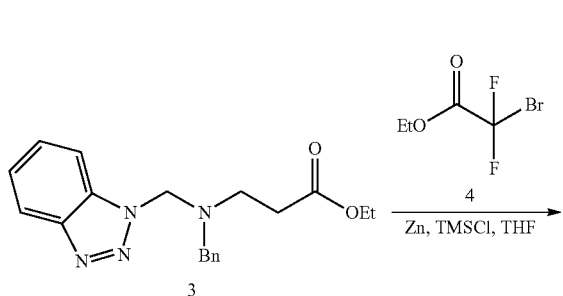

-continued

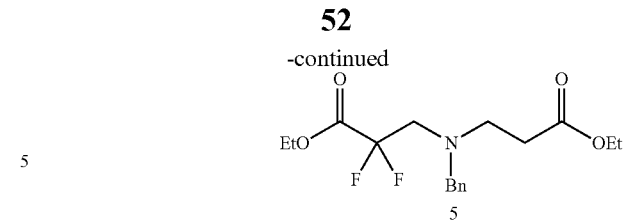

To a solution of activated Zn dust (6.2 g, 0.096 mol) in dry THF (150 mL) was added TMSCl (5.7 g, 0.053 mol), and the solution was stirred at rt for 10 minutes. Then compound 4 (9.7 g, 0.048 mol) was added slowly while the temperature was keep below 30° C. A solution of compound 3 (16 g, 0.048 mol) in THF (100 mL) was added. The mixture was stirred at 28° C. for 16 h. The reaction mixture was poured into water and the precipitate was filtered. The filtrate was diluted with EtOAc (100 mL), washed with 1N HCl and water. The organic layer was dried over $Na_2SO_4$ and concentrated in vacuum to give the crude product, which was purified by column chromatography on silica gel (PE:EA=1:1) to give compound 5 (12.4 g, yield 78%). LCMS: 344 [M+1]. $^1$H NMR (400 MHz, CDCl$_3$) δ 7.45-7.16 (m, 5H), 4.31 (d, J=7.3 Hz, 2H), 4.18-4.03 (m, 4H), 3.20 (s, 2H), 3.01-2.84 (m, 2H), 2.53-2.37 (m, 2H), 1.34 (t, J=7.2 Hz, 3H), 1.25 (t, J=7.2 Hz, 3H).

1.1.3 Preparation of Compound 6

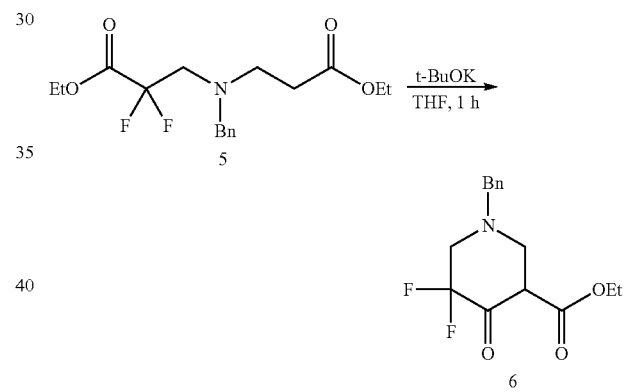

To a solution of compound 5 (8.0 g, 23.2 mmol) in THF (200 mL) was added t-BuOK (3.90 g, 34.9 mmol) slowly under 0° C. Then the mixture was stirred at rt for 1 hour. The mixture was quenched with water and extracted by EtOAc (100 mL). The organic layer was dried over $Na_2SO_4$ and concentrated in vacuum to give the crude product compound 6. LCMS: 298 [M+1].

1.1.4 Preparation of Compound 7

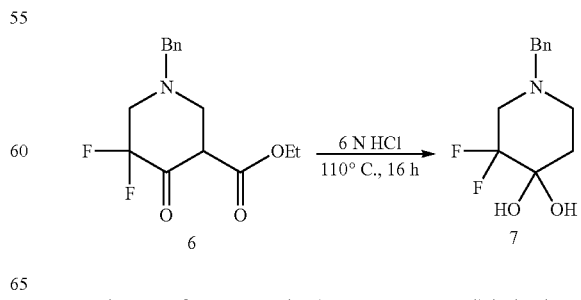

A mixture of compound 6 (6.5 g, 21.9 mmol) in hydrochloric acid (6 N, 180 mL) was stirred at 110° C. for 16 hours. The mixture was adjusted pH to 8 with 1 N aqueous NaOH solution. The mixture was extracted with EtOAc (180 mL), the organic layer was dried over Na₂SO₄ and concentrated in vacuo to give the crude product compound 7 as white solid. LCMS: 244 [M+1].

1.1.5 Preparation of Compound 8

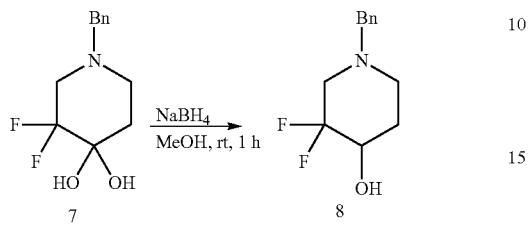

To a solution of compound 7 (5.3 g, 21.4 mmol) in MeOH (80 mL) was added NaBH₄ (1.2 g, 32.1 mmol) at 0° C. and the solution was stirred for 2 h, the solution was washed with water and extracted by EtOAc (180 mL), the organic layer was dried over Na₂SO₄ and concentrated in vacuo to give the crude product compound 8 (4.8 g, yield 96%) as colorless liquid. LCMS: 228 [M+1]. ¹H NMR (400 MHz, CDCl₃) δ 7.34 (s, 5H), 3.92-3.78 (m, 1H), 3.63 (s, 2H), 2.97-2.82 (m, 1H), 2.75-2.51 (m, 2H), 2.47-2.29 (m, 2H), 2.06-1.97 (m, 1H), 1.89-1.82 (m, 1H).

1.1.6 Preparation of Compound 9

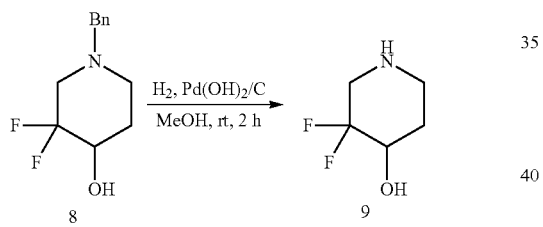

A mixture of compound 8 (2.0 g, 8.8 mmol) and Pd(OH)₂/C (0.2 g) in MeOH (80 mL) was stirred for 2 h at rt under H₂ balloon. The reaction mixture was filtered and the filtrate was concentrated in vacuum to give the crude product compound 9 (1.01 g, yield 84%) as white solid.

1.1.7 Preparation of Compounds 1732-1734

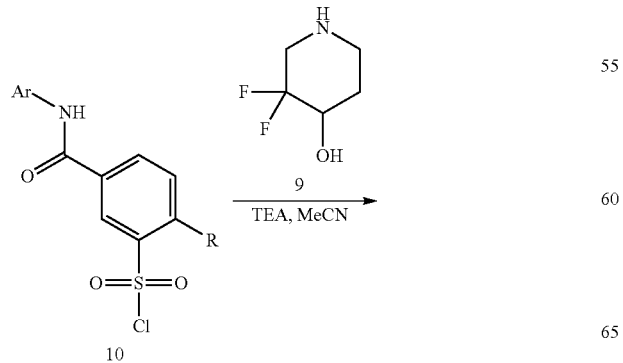

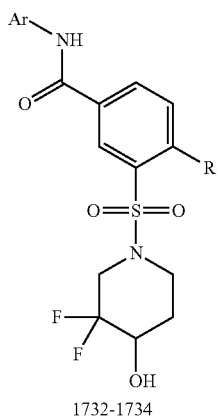

1732-1734

To a solution of compound 10 (0.3 mmol) in MeCN (3 mL) was added compound 9 (0.3 mmol) at rt, followed by Et₃N (30 mg, 0.33 mmol), and the mixture was stirred at rt for 2 h. The mixture was diluted with CH₂Cl₂ (20 mL) and washed with water. The organic phase was concentrated in vacuo to give the crude product, which was purified by prep-HPLC to give the desired product.

2 Procedure for Preparation of Compounds 1963-1968
2.1 Preparation of Compound 1968

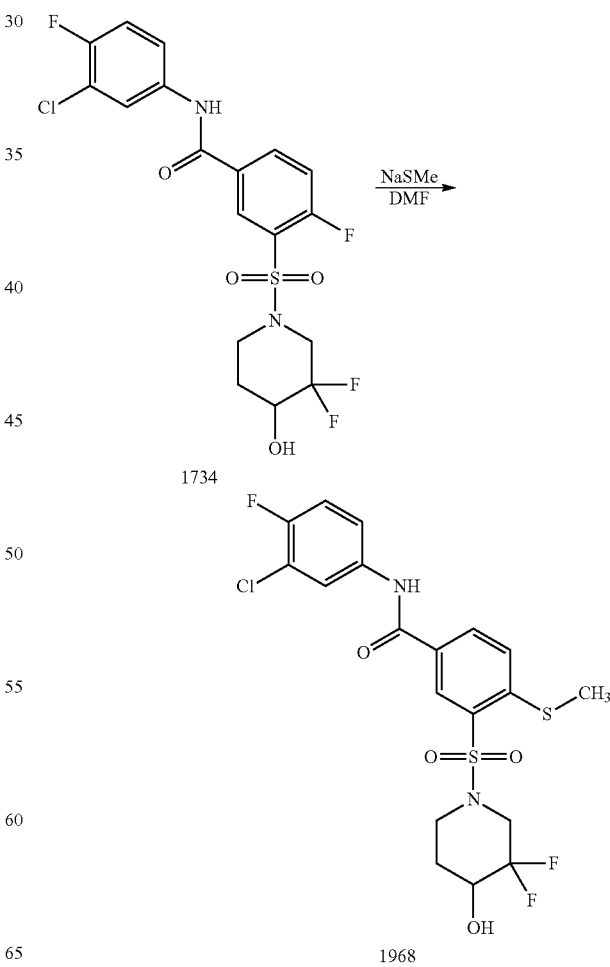

To a solution of compound 1 (210 mg, 0.45 mmol) in DMF (5 mL) was added NaSMe (315 mg, 4.5 mmol) at rt and stirred for 2 hours. The mixture was diluted with water (30 mL) and extracted with EtOAc (40 mL). The organic layer was dried over Na$_2$SO$_4$ and concentrated in vacuo to give the crude product, which was purified by pre-HPLC to give compound 1968 (120 mg, yield 41%) as white solid.

2.2 Preparation of Compound 1963

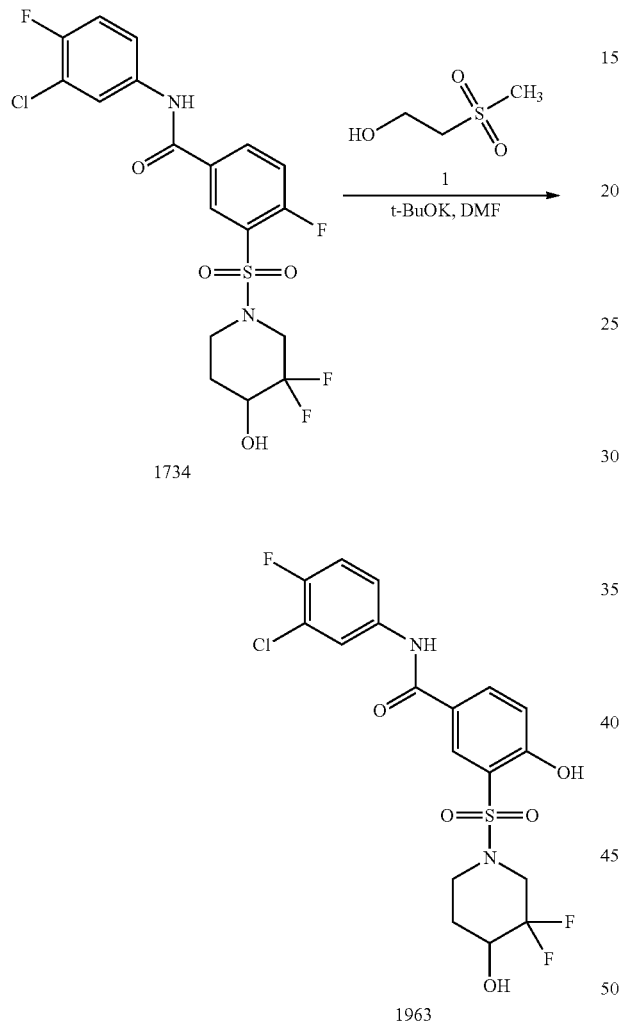

2.3 Preparation of Compound 1964

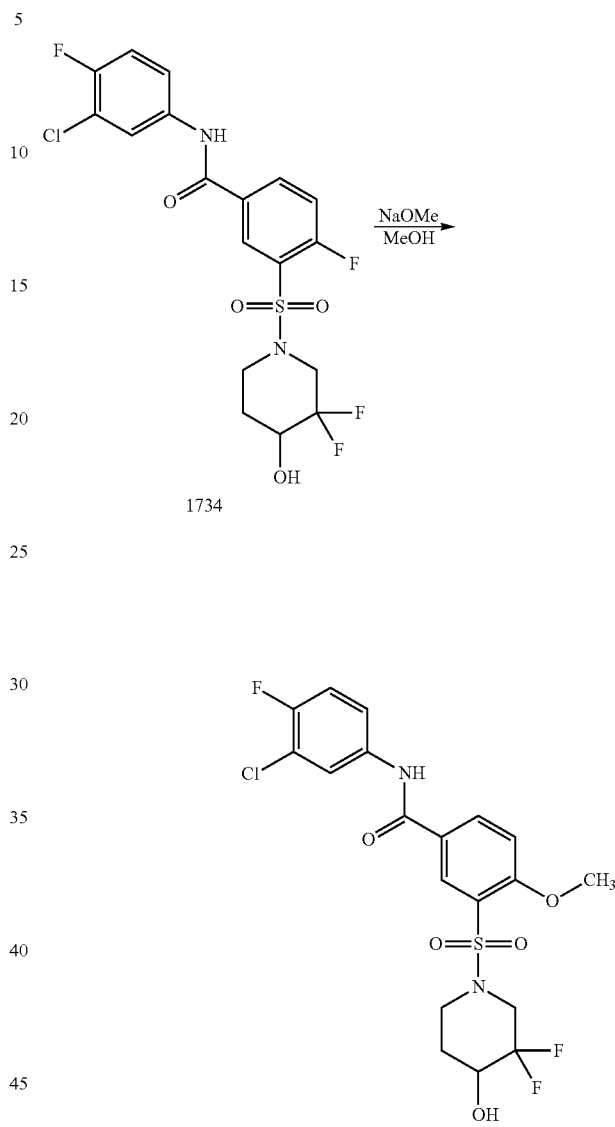

To a solution of 2-(methylsulfonyl)ethanol (52 mg, 0.42 mmol) in DMF (5 mL) was added t-BuOK (109 mg, 0.98 mmol) in an ice-water bath, and the mixture stirred for 10 mins. Compound 1734 (65 mg, 0.14 mmol) was added, and the mixture was stirred at rt for 16 h. LCMS detected the reaction was complete. The reaction mixture was quenched with water (30 mL), and extracted with EtOAc (30 mL). The organic layer was dried over Na$_2$SO$_4$ and concentrated in vacuum to give the crude product which was purified by pre-HPLC to give compound 1963 (10 mg, yield 15%) as white solid.

To a solution of compound 1734 (15.0 mg, 0.032 mmol) in MeOH (2 mL) was added NaOMe (17.2 mg, 0.32 mmol), and the mixture was stirred at 60° C. for 16 hours. The reaction was quenched with NH$_4$Cl solution (2 mL). The resulting mixture was concentrated in vacuo. The residue was diluted with water (5 mL), and extracted with EA (20 mL). The organic layer was dried over Na$_2$SO$_4$ and concentrated in vacuum to give the crude product, which was purified by pre-HPLC to give compound 1964 (10 mg, yield 67%) as white solid.

2.4 Preparation of Compound 1965

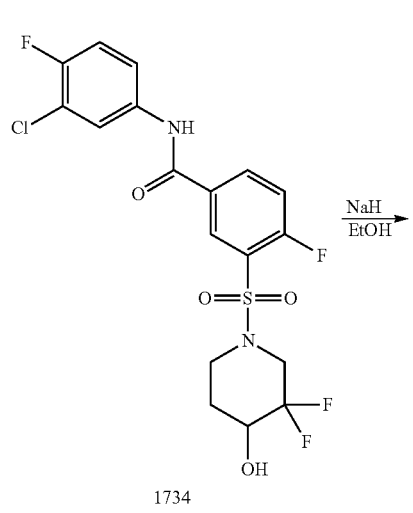

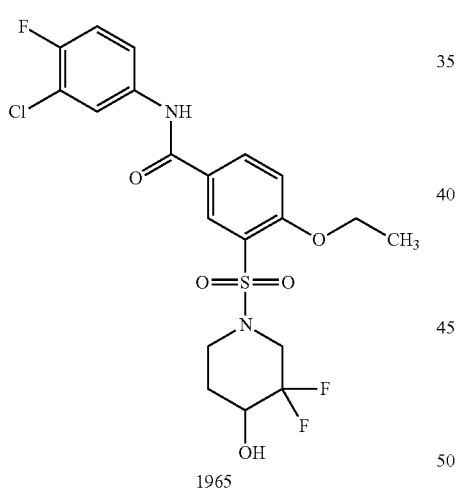

To a solution of compound 1734 (100 mg, 0.22 mmol) in EtOH (5 mL) was added NaH (86 mg, 2.2 mmol), and the mixture was stirred at 60° C. for 16 hours. The mixture was quenched with water (2 mL) and concentrated in vacuo. The residue was diluted with water (10 mL) and extracted with EtOAc (30 mL). The organic layer was dried over $Na_2SO_4$ and concentrated in vacuo to give the crude product, which was purified by pre-HPLC to give compound 1965 (65 mg, yield 61%) as white solid.

2.5 Preparation of Compound 1966

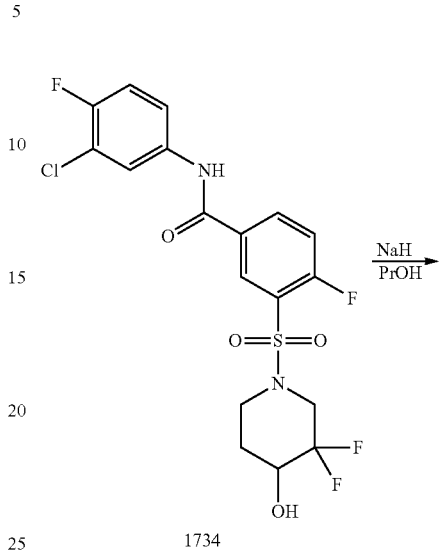

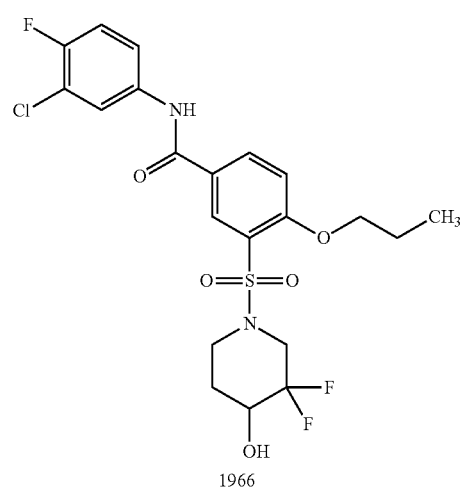

To a solution of compound 1734 (50 mg, 0.11 mmol) in n-propyl alcohol (2 mL) was added NaH (41 mg, 1.1 mmol), then the mixture was stirred at 60° C. for 16 hours. The mixture was quenched with water (5 mL) and concentrated in vacuo. The residue was diluted with water (10 mL) and extracted with EtOAc (30 mL). The organic layer was dried over $Na_2SO_4$ and concentrated in vacuo to give the crude product, which was purified by pre-HPLC to give compound 1966 (30 mg, yield 56%) as white solid.

2.6 Preparation of Compound 1967
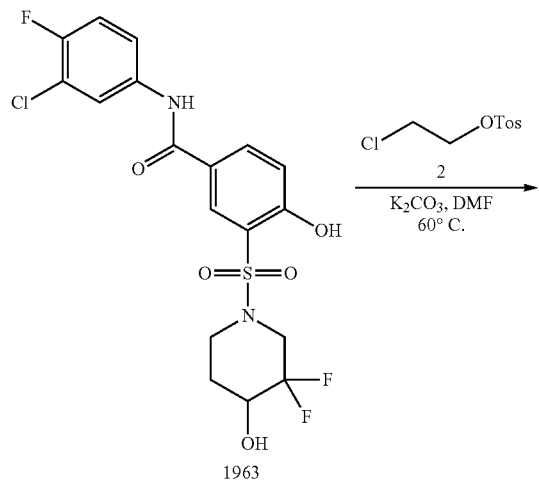
1963
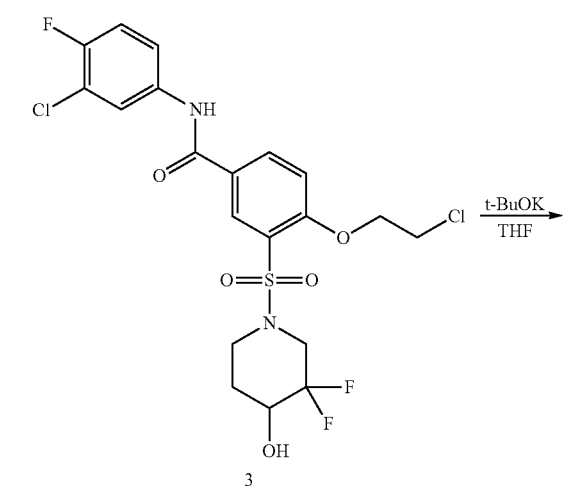
3
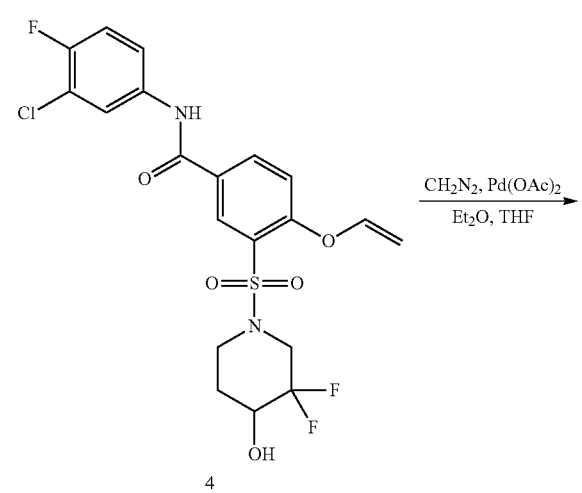
4
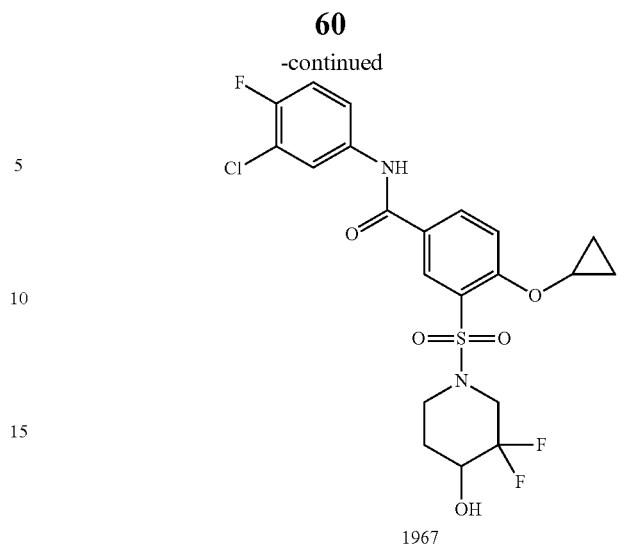
1967
2.6.1 Preparation of Compound 3
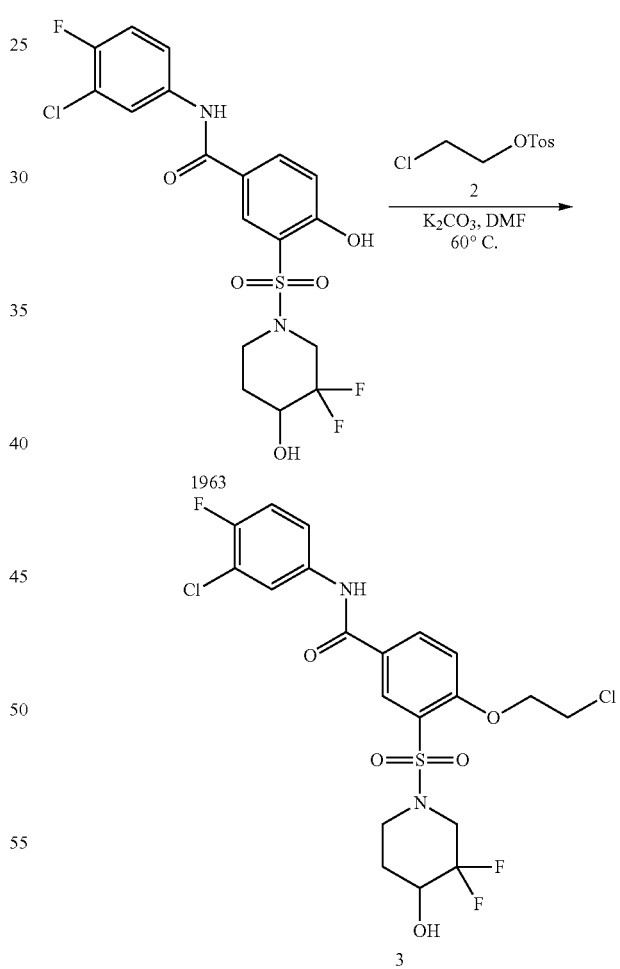
3
To a solution of compound 1963 (1.2 g, 2.58 mmol) in DMF (20 mL) was added compound 2 (907 mg, 3.88 mmol) and $K_2CO_3$ (712 mg, 5.16 mmol), then the mixture was stirred at 90° C. for 16 hour. The mixture was diluted with water (30 mL) and extracted with EtOAc (80 mL). The organic layer was dried over $Na_2SO_4$ and concentrated in vacuo to give the crude product, which was purified by column chromatography on silica gel (PE:EA=1:1) to give compound 3 (1.2 g, yield 73.5%) as yellow solid. LCMS: 527/529 [M+1].

2.6.2 Preparation of Compound 4

2.6.3 Preparation of Compound 1967

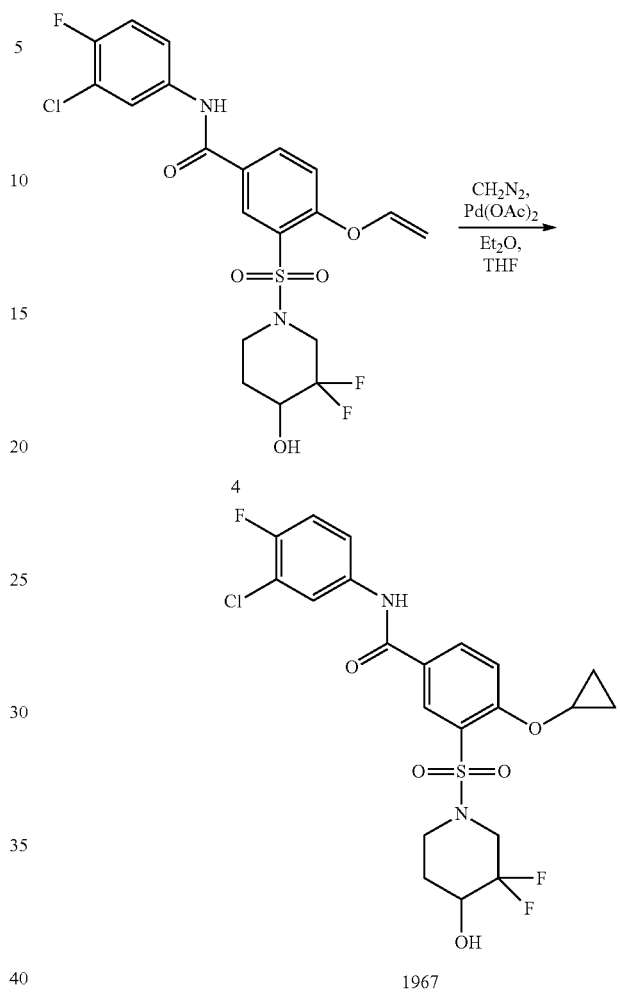

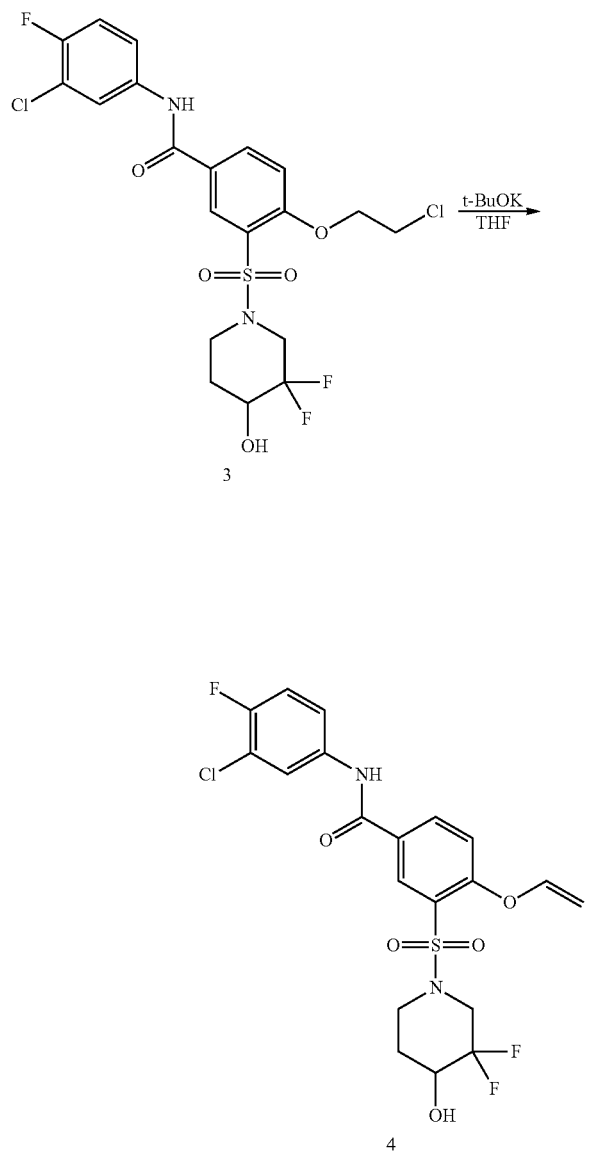

To a solution of compound 4 (165 mg, 2.33 mmol) in Et$_2$O (4 mL) was added CH$_2$N$_2$/Et$_2$O (40 mL) slowly at −78° C. The mixture was stirred at this temperature for 2 h, and then allowed to warm to room temperature and stirred for another 1 hour. Then HCl solution (10 mL, 1N) was added to quench the reaction. The organic phase was separated and the aqueous was extracted with EtOAc (20 mL), the combined organic layer was dried over Na$_2$SO$_4$ and concentrated in vacuo to give the crude product, which was purified by pre-HPLC to give compound 1967 (30 mg, yield 17.6%) as white solid.

3 Procedure for Preparation of Compounds 1993-1995

3.1 General Scheme:

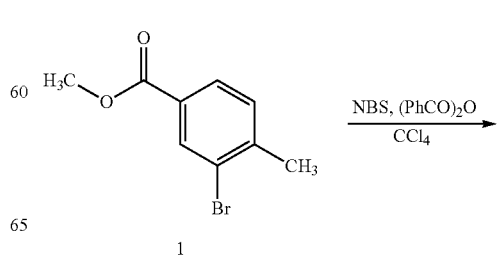

To a solution of compound 3 (1.0 g, 1.90 mmol) in THF (40 mL) was added t-BuOK (425 mg, 3.8 mmol), then the solution was stirred at rt for 2 hour. The mixture was quenched with water (30 mL) and extracted with EtOAc (40 mL). The organic layer was dried over Na$_2$SO$_4$ and concentrated in vacuo to give the crude product, which was purified by column chromatography on silica gel (PE:EA=1:1) to give compound 4 (410 mg, yield 44%) as white solid. LCMS: 490/492 [M+1].

-continued

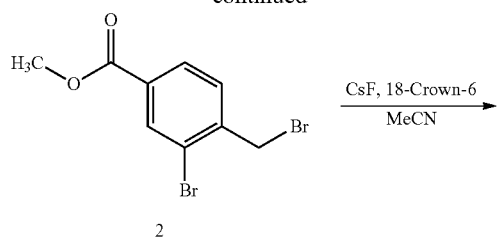

2

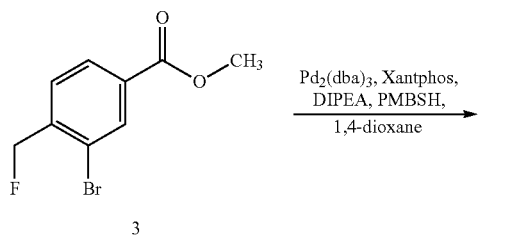

3

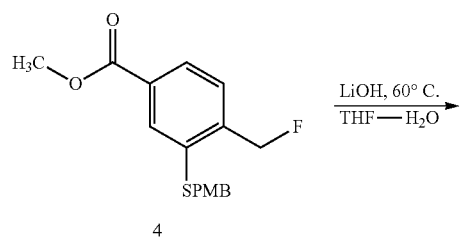

4

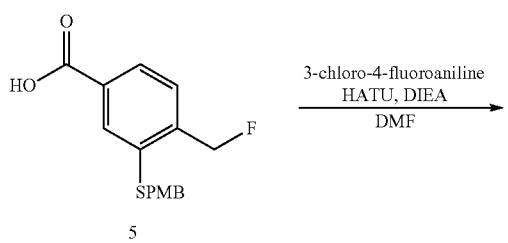

5

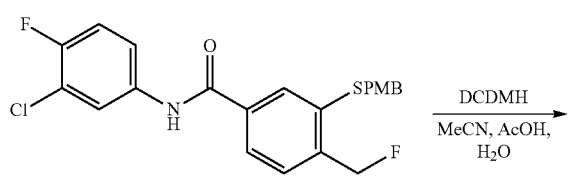

6

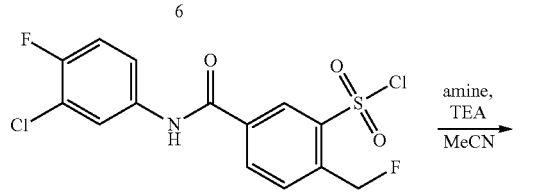

7

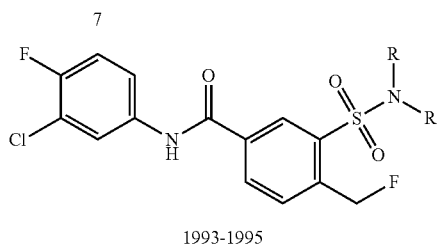

1993-1995

3.1.1 Preparation of Compound 2

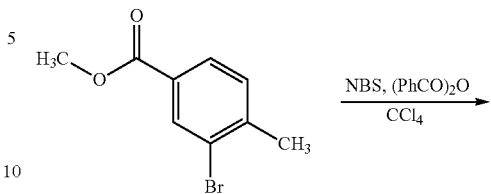

1

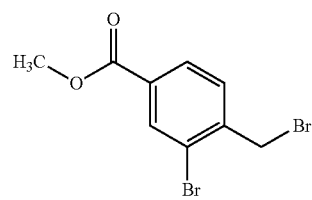

2

A mixture of compound 1 (40 g, 0.17 mol), NBS (28 g, 0.16 mol) and (PhCO)$_2$O (3.8 g, 17 mmol) in CCl$_4$ (400 mL) was heated to reflux for 2 hours. Then the mixture was concentrated under vacuo, and the residue was purified by column chromatography (PE: EtOAc=20:1) to give the compound 2 (33 g, 64%). $^1$H NMR (400 MHz, CDCl$_3$) δ 8.27 (d, J=1.5 Hz, 1H), 7.98 (dd, J=1.5, 8.0 Hz, 1H), 7.55 (d, J=8.0 Hz, 1H), 4.63 (s, 2H), 3.94 (s, 3H).

3.1.2 Preparation of Compound 3

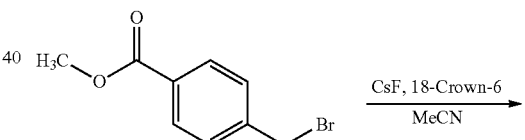

2

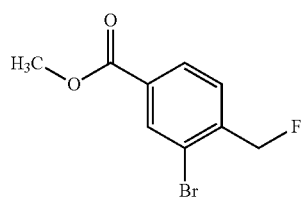

3

To a solution of compound 2 (33 g, 0.11 mol) in MeCN (500 mL) was added CsF (84 g, 0.55 mol) and 18-crown-6 (3 g). The mixture was stirred at 60° C. for 16 hours. The mixture was diluted with EA and water. The organic phase was concentrated in vacuo to give the crude product, which was purified through column chromatography to give the desired product compound 3 (17.2 g, 64%). $^1$H NMR (400 MHz, CDCl$_3$) δ 8.25 (s, 1H), 8.06 (d, J=8.0 Hz, 1H), 7.58 (d, J=8.0 Hz, 1H), 5.53 (d, J=46.8 Hz, 2H), 3.96 (s, 3H).

3.1.3 Preparation of Compound 4

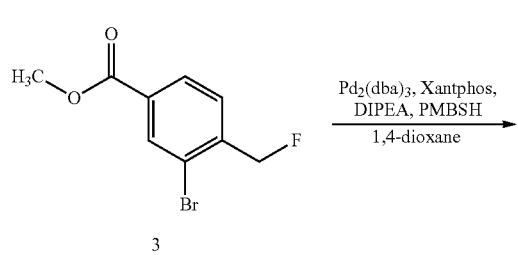

A mixture of compound 3 (17.2 g, 0.07 mol), PMBSH (17.1 g, 0.11 mol), Pd$_2$(dba)$_3$ (3.2 g, 3.5 mmol), Xantphos (2 g, 3.5 mmol) and DIPEA (18 g, 0.14 mol) in 1,4-dioxane (300 mL) was heated to 100° C. for 16 hours. Then the mixture was concentrated under vacuo, and purified by column chromatography (PE:AcOEt=10:1) to give the compound 4 (19.8 g, 89%). LCMS: 321 [M+1].

3.1.4 Preparation of Compound 5

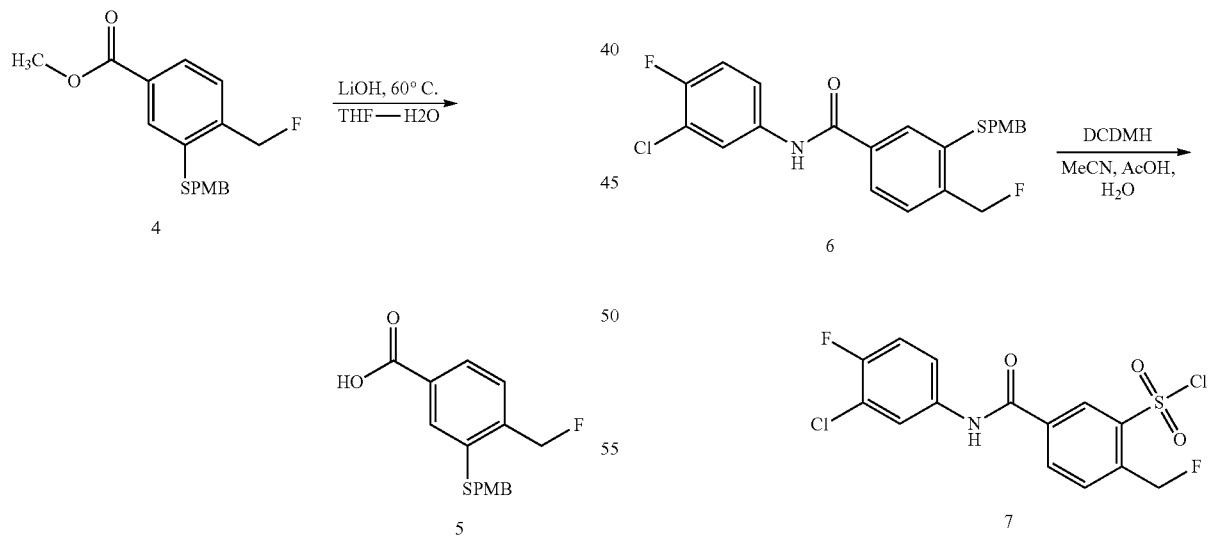

A mixture of compound 4 (3.21 g, 10 mmol) and LiOH (4.20 g, 100 mmol) in THF/H$_2$O (50 mL/10 mL) was heated to 60° C. for 4 hours. The reaction mixture was adjusted to pH=6.0 with HCl (1N), and extracted with EtOAc. The organic phase was dried over Na$_2$SO$_4$ and concentrated in vacuo to give the compound 5 (2.45 g, 80%). LCMS: 307 [M+1].

3.1.5 Preparation of Compound 6

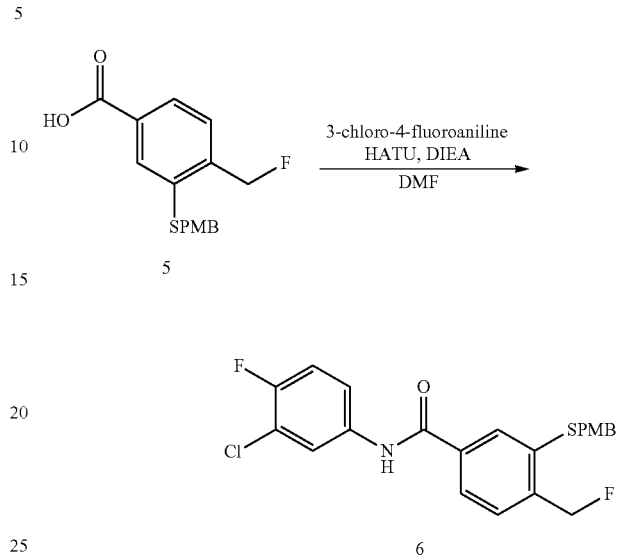

A mixture of compound 6 (1 g, 3.26 mmol), HATU (1.24 g, 3.26 mmol), DIPEA (0.84 g, 6.52 mmol), and 3-chloro-4-fluoroaniline (0.47 g, 3.26 mmol) in DMF (10 mL) was stirred at rt for 4 hours. The mixture was diluted with AcOEt and water, and combined organic layers were dried over Na$_2$SO$_4$ and concentrated in vacuo. Then the residue was purified by column chromatography (PE: AcOEt=5:1) to give the compound 5 (1.1 g, 78%). LCMS: 434/436 [M+1].

3.1.6 Preparation of Compound 7

To a solution of compound 6 (150 mg, 0.35 mmol) in MeCN (8 mL), AcOH (0.1 mL) and H$_2$O (0.2 mL) was added DCDMH (109 mg, 0.55 mmol) at −15° C. and stirred for 4 hours. Then the mixture was diluted with water and extracted with DCM. The combined organic layer was dried over Na$_2$SO$_4$ and concentrated in vacuo to give a crude product (133 mg, crude), used directly in the next step.

3.1.7 Preparation of Compound 1995

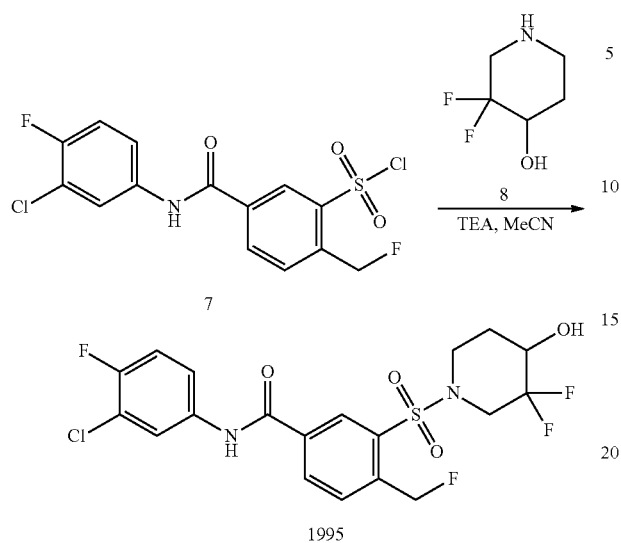

To a solution of compound 7 (134 mg, 0.35 mmol, crude) in MeCN (2 mL) was added TEA (106 mg, 1.05 mmol) and compound 8 (48 mg, 0.35 mmol). The resulting mixture was stirred at rt until the starting material was consumed. The solvent was removed and the residue was purified by pre-HPLC (FA) to give desired compound 1995. LCMS: 481/483 [M+1].

Compounds 1993 and 1994 were prepared according to the procedure of compound 1995.

4 Procedure for Preparation of Compounds 2051 and 2059

4.1 General Scheme:

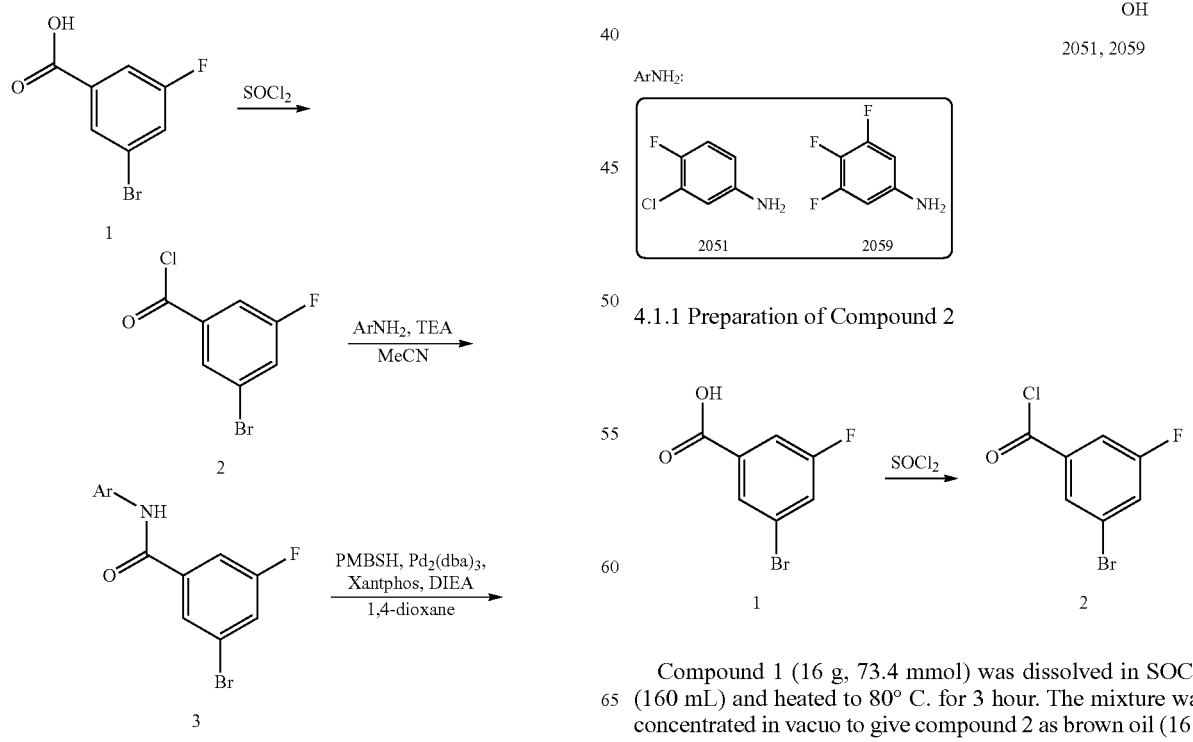

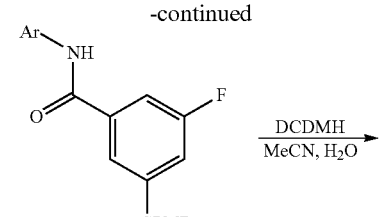

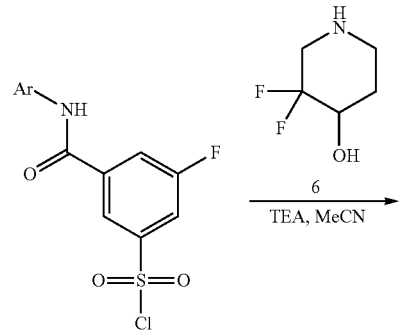

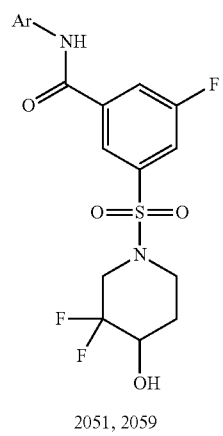

ArNH$_2$:

4.1.1 Preparation of Compound 2

Compound 1 (16 g, 73.4 mmol) was dissolved in SOCl$_2$ (160 mL) and heated to 80° C. for 3 hour. The mixture was concentrated in vacuo to give compound 2 as brown oil (16.8 g, 97.1%).

4.1.2 Preparation of Compound 4

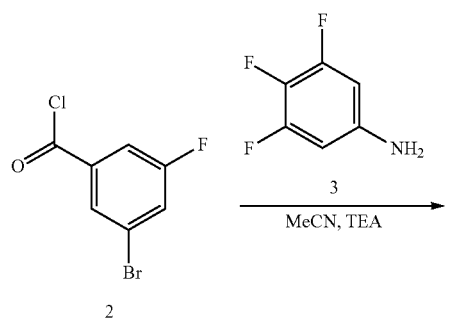

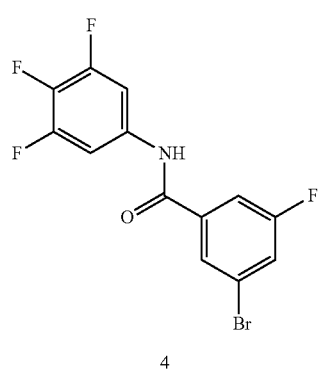

To a solution of compound 3 (5.2 g, 35.7 mmol) in MeCN (130 mL) added TEA (7.2 g, 171.4 mmol) followed by compound 2 (8.4 g, 35.7 mmol). The mixture was stirred at 16° C. for 2 hour. Filtrated, the white solid was collected to give the desired product. LCMS: 348/350 [M+1].

4.1.3 Preparation of Compound 5

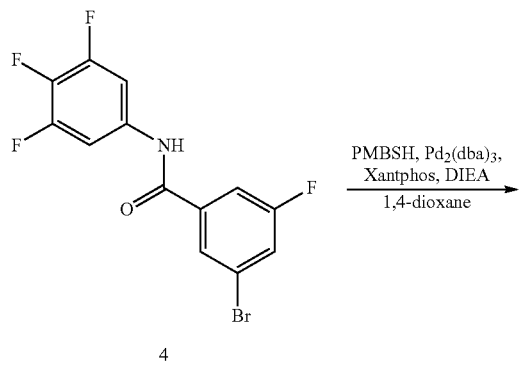

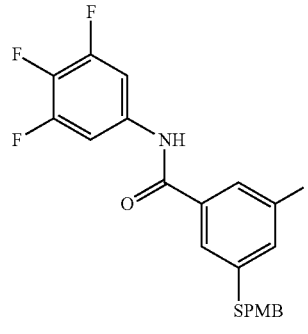

A mixture of compound 4 (4.0 g, 11.56 mmol), PMBSH (2.7 g, 17.34 mmol), $Pd_2(dba)_3$ (529.3 mg, 058 mmol), Xantphos (671.2 mg, 1.16 mmol) and DIEA (2.98 g, 23.12 mmol) in dioxane (80 mL) was heated to 110° C. for 16 hour under $N_2$. The mixture was concentrated in vacuo to give the crude product, which was purified by column chromatography to give compound 5 as yellow solid (3.5 g, 72%). LCMS: 422 [M+1].

4.1.4 Preparation of Compound 6

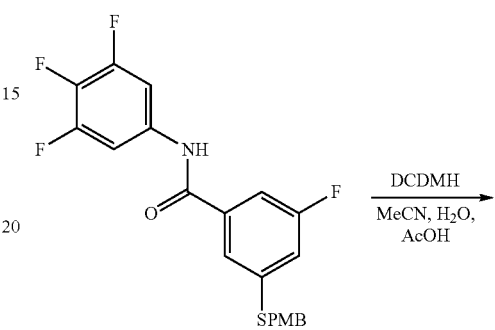

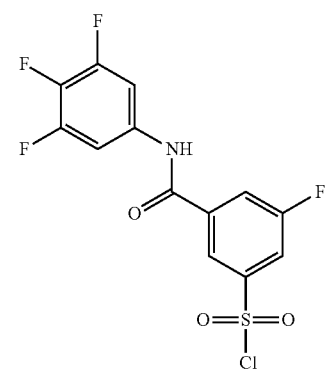

To a solution of compound 5 (100 mg, 0.24 mmol) in $MeCN/H_2O/HOAc$ (90:1:2) (30 mL) added DCDMH (74.9 mg, 0.38 mmol) portion-wise, while keeping inner temperature between −5~0° C. Then the mixture was stirred at 0° C. for 2 hour. The mixture was used in the next step directly without further purification.

4.1.5 Preparation of Compound 2059

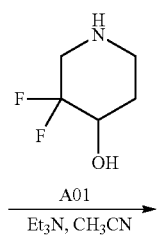

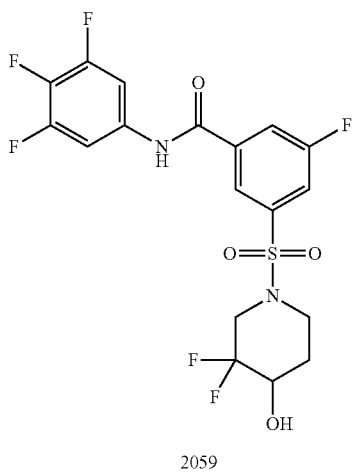

2059

To a solution of compound 6 (93 mg crude, 0.25 mmol) in MeCN (5 mL) was added compound A01 (34 mg, 0.25 mmol) and Et₃N (25 mg) at room temperature. The formed mixture was stirred for 2 hours. The mixture was concentrated in vacuo. The residue was diluted with water and extracted with EA. The organic phase was concentrated in vacuo and the residue was purified via acid prep-HPLC to give the desired product compound 2059 (4.33 mg, 5.5%). ¹H NMR (400 MHz, CD₃OD) δ 8.22 (s, 1H), 8.05 (d, J=8.5 Hz, 1H), 7.87-7.82 (m, 1H), 7.63 (dd, J=6.4, 9.9 Hz, 2H), 3.90-3.80 (m, 1H), 3.60-3.39 (m, 2H), 3.31-3.19 (m, 2H), 1.97 (ddd, J=4.4, 9.0, 13.4 Hz, 1H), 1.84 (tdd, J=3.2, 6.8, 10.2 Hz, 1H). LCMS: 469[M+1].

Compound 2051 were prepared following the same procedure as compound 2059.

Example

HBV Assembly Assay

The fluorescence quenching in vitro assembly HBV assay was developed according to a method described by Zlotnick and coworkers (Nature Biotechnology 2006, 24:358). The assay is based on the observation that the C-termini of the HBV core protein cluster together during capsid formation. This assay utilizes a mutant C150 HBV capsid protein where all wild-type cysteines are mutated to alanines, but a C-terminal cysteine residue is preserved and is labeled with fluorescent BoDIPY-FL dye. HBV C150Bo protein is highly fluorescent, however the fluorescence is drastically reduced during the capsid assembly process. Thus, the assay measures the ability and potency of test compounds to modulate capsid assembly by monitoring the fluorescence of the labeled capsid C150Bo protein.

In a typical assay, the mutant HBV C150 protein (amino acids 1-150, C49A, C61A, C107A, 150C) is cloned into a T7 RNA-polymerase based expression vector, expressed in E. coli and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature.

To determine the effect on capsid assembly, each test compound is initially screened in at least 4 different concentrations in duplicates. Primary hits are compounds that show activity in the assembly assay at 10 µM. Identified primary hits are confirmed in follow-up studies as described elsewhere herein. Known modulators of HBV CA assembly, such as HAP-1 and BAY 41-4109, are used as control compounds in these experiments and exhibited $EC_{50}$ values consistent with the literature. $EC_{50}$ values for test compounds are determined via analysis of the dose-response curve.

Selected compounds of the invention were assayed in the HBV assembly assay, as described above. The assembly assay was conducted in 96-well plate format. The assembly reactions were carried out in 50 mM Hepes buffer, pH 7.5 and 150 mM NaCl. The compounds were pre-incubated with the HBV CA protein for 15 min, and the assembly reactions were initiated by addition of NaCl. The reaction was allowed to continue for 1 hour at room temperature. The 96-well plate assembly assay consistently had Z' factors greater than 0.7 and were robust and reproducible both from plate-to-plate and day-to-day.

To determine the effect on capsid assembly, each test compound was initially screened at 5 different concentrations: about 30 µM, 10 µM, 3 µM, 1 µM, and 0.3 µM in duplicates. Primary hits were compounds that show >50% activity in the assembly assay at about 10 µM and a representative group of these active compounds is shown in Table 2.

TABLE 2

| HBV assembly assay ('+' indicates >50% activity at about 10 (µM) ||
|---|---|
| Compound | Activity |
| 1732 | + |
| 1733 | + |
| 1734 | + |
| 1963 | + |
| 1964 | + |
| 1965 | + |
| 1967 | + |
| 1995 | + |

Example

Dot-Blot Assay

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the Kodak films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CellTiter Blue-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CellTiter Blue. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CellTiter Blue kit, Promega).

Selected compounds were tested for their activity and toxicity in cellular assay. In the first anti-viral assay, the ability of compounds to inhibit HBV replication in an HBV-producing hepatoma cell line using the dot-blot method was evaluated.

Confluent monolayers of HepG2-2.2.15 cells were incubated with complete medium containing various concentrations of a test compound. Three days later, the culture medium was replaced with fresh medium containing the appropriately diluted test compound. Six days following the initial administration of the test compound, the cell culture supernatant was collected, and cell lysis was performed. The samples were applied onto Nylos membranes and DNA was immobilized to the membrane by UV cross-linking. After pre-hybridization, the HBV probe was added and the hybridization was performed overnight. The membranes were exposed to the Kodak films; antiviral activity was calculated from the reduction in HBV DNA levels ($EC_{50}$). The $EC_{50}$ for antiviral activity was calculated from the dose response curves of active compounds. Assay performance over time was monitored by the use of the standard positive control compounds ETV, BAY 41-4109, and HAP-1. Results are illustrated in Table 3.

Cytotoxicity ($CC_{50}$) was measured in this same HepG2-2.2.15 cell line using a CellTiter Blue-based cytotoxicity assay employed as recommended by manufacturer (Promega).

TABLE 3

| "Activity" represents activity in dot-blot-assay ('+' indicates >50% activity at 10 (μM)) | |
|---|---|
| Compound | Activity |
| 1732 | + |
| 1733 | + |
| 1734 | + |
| 1995 | + |

Example

Prevention of HBV Pre-Genomic RNA (pgRNA) Incorporation

The anti-viral activity of the compounds of the invention is assessed based on their ability to suppress both extracellular and intracellular HBV DNA production in two different cell culture models of HBV replication. To assess if these effects are due to disruption of intracellular capsid assembly, a particle-gel assay that allows quantitation of intracellular viral capsids, as well as encapsidated pre-genomic RNA and DNA, is performed. The assay relies on agarose gel separation of viral capsid from free capsid/core subunits and viral pg-RNA and DNA.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula II:

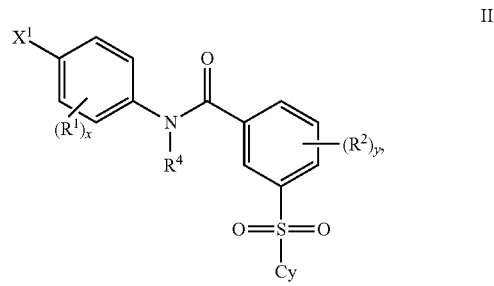

II or a pharmaceutically acceptable salt thereof;
wherein
$X^1$ is halo;
$R^4$ is H or $C_1$-$C_3$ alkyl;
each $R^1$ is halo;
each $R^2$ is halo;

Cy is

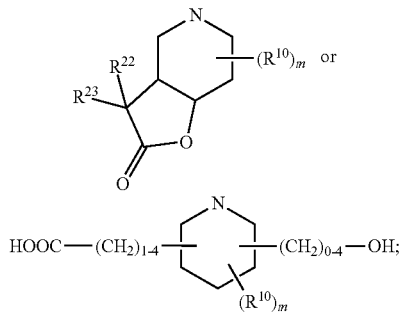

$R^{22}$ and $R^{23}$ are, independently at each occurrence, H or halo;
m is 0;
x is 1; and
y is 1, 2, 3, or 4.

2. A pharmaceutical composition comprising a compound of claim 1, or a pharmaceutically acceptable salt thereof, together with a pharmaceutically acceptable carrier.

3. A method of treating an HBV infection in an individual in need thereof, comprising administering to the individual a therapeutically effective amount of a compound according to claim 1.

4. The method of claim 3, further comprising administering to the individual at least one additional therapeutic agent selected from the group consisting of a HBV polymerase inhibitor, interferon, viral entry inhibitor, viral maturation inhibitor, BAY 41-4109, reverse transcriptase inhibitor, a TLR-agonist, AT-61 ((E)-N-(1-chloro-3-oxo-1-phenyl-3-(piperidin-1-yl)prop-1-en-2-yl)benzamide), and AT-130 ((E)-N-(1-bromo-1-(2-methoxyphenyl)-3-oxo-3-(piperidin-1-yl)prop-1-en-2-yl)-4-nitrobenzamide), and a combination thereof.

5. The method of claim 3, further comprising administering to the individual at least one HBV vaccine, a nucleoside HBV inhibitor, an interferon or any combination thereof.

6. A method of treating an HBV infection in an individual in need thereof, comprising reducing the HBV viral load by administering to the individual a therapeutically effective amount of a compound according to claim 1, or a compound according to claim 1 in combination with a reverse transcriptase inhibitor; and further administering to the individual a therapeutically effective amount of HBV vaccine.

7. The method of claim 3 further comprising monitoring the HBV viral load of the subject, and wherein the method is carried out for a period of time such that the HBV virus is undetectable.

8. The compound of claim 1, wherein the compound is:

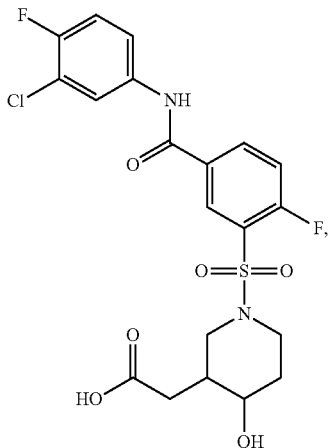 [SMILES: O=C(O)CC1CN(S(=O)(=O)c2cc(C(=O)Nc3ccc(F)c(Cl)c3)ccc2F)CCC1O]

or a pharmaceutically acceptable salt thereof.

9. The compound of claim 1, wherein the compound is:

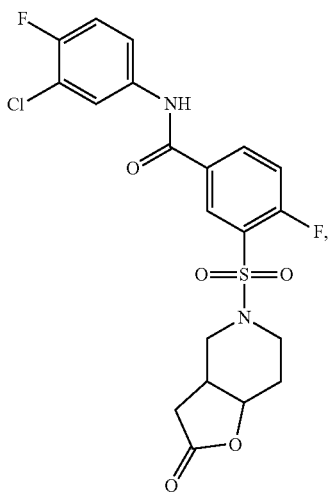 [SMILES: O=C1CC2CN(S(=O)(=O)c3cc(C(=O)Nc4ccc(F)c(Cl)c4)ccc3F)CCC2O1]

or a pharmaceutically acceptable salt thereof.

* * * * *